US011992183B2

(12) United States Patent
Landey et al.

(10) Patent No.: US 11,992,183 B2
(45) Date of Patent: May 28, 2024

(54) SHAFT ACTUATING HANDLE

(71) Applicant: Auris Health, Inc., Redwood City, CA (US)

(72) Inventors: Casey Teal Landey, San Francisco, CA (US); Ryan Jeffrey Connolly, San Carlos, CA (US); Brett Andrew Snyder, Campbell, CA (US)

(73) Assignee: Auris Health, Inc., Redwood City, CA (US)

( * ) Notice: Subject to any disclaimer, the term of this patent is extended or adjusted under 35 U.S.C. 154(b) by 289 days.

(21) Appl. No.: 17/037,296

(22) Filed: Sep. 29, 2020

(65) Prior Publication Data

US 2021/0008341 A1 Jan. 14, 2021

Related U.S. Application Data

(63) Continuation of application No. 15/937,516, filed on Mar. 27, 2018, now Pat. No. 10,792,466.

(Continued)

(51) Int. Cl.
*A61B 1/00* (2006.01)
*A61B 1/005* (2006.01)
(Continued)

(52) U.S. Cl.
CPC ...... *A61B 1/00147* (2013.01); *A61B 1/00149* (2013.01); *A61B 1/0052* (2013.01);
(Continued)

(58) Field of Classification Search
CPC ...... A61B 2017/003; A61B 2017/0031; A61B 17/00234; A61B 1/0052; A61B 1/00149;
(Continued)

(56) References Cited

U.S. PATENT DOCUMENTS 3,763,860 A 10/1973 Clarke
4,040,413 A 8/1977 Ohshiro
(Continued)

FOREIGN PATENT DOCUMENTS

CN 101443069 5/2009
CN 100515347 7/2009
(Continued)

OTHER PUBLICATIONS

Final Rejection for U.S. Appl. No. 15/937,516, dated Sep. 23, 2019, 14 pages.

(Continued)

*Primary Examiner* — Pamela M. Bays
*Assistant Examiner* — Amanda L Steinberg
(74) *Attorney, Agent, or Firm* — Chang & Hale LLP

(57) ABSTRACT

Certain aspects relate to a handle mechanism that permits control of linear motion of a shaft secured within the handle via two different interfaces for actuating the linear motion. In some aspects, a rotational interface can allow for fine control linear positioning of the shaft, for example by allowing a user to rotate the rotational interface to extend or retract the shaft. In some aspects, a plunging interface can enable a faster linear motion, for example by implementing a biasing mechanism that releases to drive rapid linear motion.

20 Claims, 17 Drawing Sheets

Related U.S. Application Data

(60) Provisional application No. 62/477,872, filed on Mar. 28, 2017.

(51) Int. Cl.
*A61B 1/267* (2006.01)
*A61B 17/00* (2006.01)
*A61B 34/30* (2016.01)
*A61M 25/01* (2006.01)

(52) U.S. Cl.
CPC ...... *A61B 1/2676* (2013.01); *A61B 17/00234* (2013.01); *A61B 34/30* (2016.02); *A61M 25/0136* (2013.01); *A61B 2017/003* (2013.01); *A61B 2034/301* (2016.02); *A61M 25/0113* (2013.01)

(58) Field of Classification Search
CPC ........... A61B 1/00147; A61M 25/0113; A61M 25/0136
See application file for complete search history.

(56) References Cited

U.S. PATENT DOCUMENTS

| | | | |
|---|---|---|---|
| 4,198,960 A | 4/1980 | Utsugi | |
| 4,470,407 A | 9/1984 | Hussein | |
| 4,532,935 A * | 8/1985 | Wang | A61B 10/0283 600/566 |
| 4,685,458 A | 8/1987 | Leckrone | |
| 4,747,405 A | 5/1988 | Leckrone | |
| 4,854,301 A | 8/1989 | Nakajima | |
| 4,898,574 A | 2/1990 | Uchiyama et al. | |
| 4,983,165 A | 1/1991 | Loiterman | |
| 5,029,574 A | 7/1991 | Shimamura et al. | |
| 5,085,659 A | 2/1992 | Rydell | |
| 5,196,023 A | 3/1993 | Martin | |
| 5,217,465 A | 6/1993 | Steppe | |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,431,649 A | 7/1995 | Mulier et al. | |
| 5,441,485 A | 8/1995 | Peters | |
| 5,449,356 A | 9/1995 | Walbrink | |
| 5,450,843 A | 9/1995 | Moll et al. | |
| 5,472,426 A | 12/1995 | Bonati et al. | |
| 5,496,267 A | 3/1996 | Drasler | |
| 5,501,667 A | 3/1996 | Verduin, Jr. | |
| 5,520,684 A | 5/1996 | Imran | |
| 5,545,170 A | 8/1996 | Hart | |
| 5,562,239 A | 10/1996 | Boiarski et al. | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,697,949 A | 12/1997 | Giurtino et al. | |
| 5,710,870 A | 1/1998 | Ohm | |
| 5,716,325 A | 2/1998 | Bonutti | |
| 5,788,667 A | 8/1998 | Stoller | |
| 5,792,165 A | 8/1998 | Klieman | |
| 5,797,900 A | 8/1998 | Madhani | |
| 5,810,770 A | 9/1998 | Chin et al. | |
| 5,893,045 A | 4/1999 | Kusama et al. | |
| 5,893,869 A | 4/1999 | Barnhart | |
| 5,897,491 A | 4/1999 | Kastenbauer et al. | |
| 5,924,175 A | 7/1999 | Lippitt | |
| 5,989,230 A | 11/1999 | Frassica | |
| 6,071,281 A | 6/2000 | Burnside et al. | |
| 6,093,157 A | 7/2000 | Chandrasekaran | |
| 6,110,171 A | 8/2000 | Rydell | |
| 6,120,476 A | 9/2000 | Fung et al. | |
| 6,120,498 A | 9/2000 | Jani et al. | |
| 6,156,030 A | 12/2000 | Neev | |
| 6,174,318 B1 | 1/2001 | Bates et al. | |
| 6,193,673 B1 * | 2/2001 | Viola | A61B 10/0275 600/568 |
| 6,206,903 B1 | 3/2001 | Ramans | |
| 6,183,435 B1 | 6/2001 | Bumbalough et al. | |
| 6,322,557 B1 | 11/2001 | Nikolaevich | |
| 6,375,635 B1 | 4/2002 | Moutafis | |
| 6,394,998 B1 | 5/2002 | Wallace et al. | |
| 6,405,078 B1 | 6/2002 | Moaddeb et al. | |
| 6,440,061 B1 | 8/2002 | Wenner et al. | |
| 6,508,823 B1 | 1/2003 | Gonon | |
| 6,522,906 B1 | 2/2003 | Salisbury et al. | |
| 6,577,891 B1 | 6/2003 | Jaross et al. | |
| 6,580,938 B1 | 6/2003 | Acker | |
| 6,676,668 B2 | 1/2004 | Mercereau et al. | |
| 6,685,698 B2 | 2/2004 | Morley et al. | |
| 6,706,050 B1 | 3/2004 | Giannadakis | |
| 6,775,404 B1 | 8/2004 | Pagoulatos et al. | |
| 7,233,820 B2 | 6/2007 | Gilboa | |
| 7,282,055 B2 | 10/2007 | Tsuruta | |
| 7,559,934 B2 | 7/2009 | Teague et al. | |
| 7,736,356 B2 | 6/2010 | Cooper et al. | |
| 7,901,348 B2 | 3/2011 | Soper et al. | |
| 7,963,911 B2 | 6/2011 | Turliuc | |
| 7,987,046 B1 | 7/2011 | Peterman | |
| 8,002,713 B2 | 8/2011 | Heske | |
| 8,038,598 B2 | 10/2011 | Khachi | |
| 8,092,397 B2 | 1/2012 | Wallace et al. | |
| 8,187,173 B2 | 5/2012 | Miyoshi | |
| 8,257,303 B2 | 9/2012 | Moll et al. | |
| 8,480,595 B2 | 7/2013 | Speeg | |
| 8,523,762 B2 | 9/2013 | Miyamoto et al. | |
| 8,540,748 B2 | 9/2013 | Murphy et al. | |
| 8,801,601 B2 | 8/2014 | Prisco et al. | |
| 8,820,603 B2 | 9/2014 | Shelton et al. | |
| 8,858,424 B2 | 10/2014 | Hasegawa et al. | |
| 8,882,660 B2 | 11/2014 | Phee et al. | |
| 8,945,163 B2 | 2/2015 | Voegele et al. | |
| 8,956,280 B2 | 2/2015 | Eversull et al. | |
| 9,345,456 B2 | 5/2016 | Tsonton et al. | |
| 9,452,276 B2 | 9/2016 | Duindam et al. | |
| 9,460,536 B2 | 10/2016 | Hasegawa et al. | |
| 9,504,604 B2 | 11/2016 | Alvarez | |
| 9,561,083 B2 | 2/2017 | Yu et al. | |
| 9,592,042 B2 | 3/2017 | Titus | |
| 9,597,152 B2 | 3/2017 | Schaeffer | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,730,757 B2 | 8/2017 | Brudniok | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |

(56) References Cited

U.S. PATENT DOCUMENTS

| | | |
|---|---|---|
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,350,390 B2 | 7/2019 | Moll et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,792,464 B2 | 10/2020 | Romo et al. |
| 10,792,466 B2 | 10/2020 | Landey et al. |
| 10,828,118 B2 | 11/2020 | Schuh et al. |
| 2002/0019644 A1 | 2/2002 | Hastings |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0085838 A1* | 4/2005 | Thompson ......... A61B 10/0275 606/170 |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106147 A1 | 5/2007 | Altmann et al. |
| 2007/0106304 A1 | 5/2007 | Hammack |
| 2007/0135803 A1 | 6/2007 | Belson |
| 2007/0156019 A1 | 7/2007 | Larkin et al. |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0293721 A1 | 12/2007 | Gilboa |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227861 A1 | 9/2009 | Ganatra et al. |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0081965 A1 | 4/2010 | Mugan et al. |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1* | 12/2010 | Keast ..................... A61M 1/84 600/567 |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0130275 A1* | 5/2012 | Chudzik ............ A61B 10/0283 600/567 |
| 2012/0138586 A1 | 6/2012 | Webster et al. |
| 2012/0138660 A1 | 6/2012 | Shelton, IV et al. |
| 2012/0209315 A1 | 8/2012 | Amat |

(56) References Cited

U.S. PATENT DOCUMENTS

| | | |
|---|---|---|
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0233908 A1 | 9/2013 | Knodel |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0334281 A1 | 12/2013 | Williams |
| 2013/0345686 A1 | 12/2013 | Brown |
| 2014/0005681 A1 | 1/2014 | Gee et al. |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1* | 2/2014 | Christopher ..... A61B 5/150412 29/428 |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276723 A1 | 9/2014 | Parihar |
| 2014/0276956 A1 | 9/2014 | Crainich |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0080879 A1 | 3/2015 | Trees |
| 2015/0101442 A1 | 4/2015 | Romo |
| 2015/0119638 A1 | 4/2015 | Yu et al. |
| 2015/0127045 A1 | 5/2015 | Prestel |
| 2015/0133960 A1 | 5/2015 | Lohmeier |
| 2015/0164522 A1 | 6/2015 | Budiman |
| 2015/0164594 A1 | 6/2015 | Romo et al. |
| 2015/0164596 A1 | 6/2015 | Romo et al. |
| 2015/0201917 A1 | 7/2015 | Snow |
| 2015/0202085 A1 | 7/2015 | Lemonis |
| 2015/0282964 A1 | 10/2015 | Beard et al. |
| 2015/0313503 A1 | 11/2015 | Seibel et al. |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0367324 A1 | 12/2016 | Sato et al. |
| 2016/0374541 A1 | 12/2016 | Agrawal et al. |
| 2017/0007337 A1 | 1/2017 | Dan |
| 2017/0049471 A1 | 2/2017 | Gaffney et al. |
| 2017/0055995 A1 | 3/2017 | Weier |
| 2017/0065227 A1 | 3/2017 | Marrs |
| 2017/0065364 A1 | 3/2017 | Schuh et al. |
| 2017/0065365 A1 | 3/2017 | Schuh |
| 2017/0071584 A1 | 3/2017 | Suigetsu et al. |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135706 A1 | 5/2017 | Frey |
| 2017/0151416 A1 | 6/2017 | Kutikov |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0265923 A1 | 9/2017 | Privitera |
| 2017/0265954 A1 | 9/2017 | Burbank |
| 2017/0290631 A1 | 10/2017 | Lee et al. |
| 2017/0303889 A1 | 10/2017 | Grim |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0055583 A1 | 3/2018 | Schuh et al. |
| 2018/0177383 A1 | 6/2018 | Noonan et al. |
| 2018/0177556 A1 | 6/2018 | Noonan |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill et al. |

(56) References Cited

U.S. PATENT DOCUMENTS

| | | |
|---|---|---|
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0093549 A1 | 3/2020 | Chin |
| 2020/0107894 A1 | 4/2020 | Wallace |
| 2020/0121502 A1 | 4/2020 | Kintz |
| 2020/0163726 A1 | 5/2020 | Tanner |
| 2020/0197112 A1 | 6/2020 | Chin |
| 2020/0222134 A1 | 7/2020 | Schuh |
| 2020/0305989 A1 | 10/2020 | Schuh |
| 2020/0315717 A1 | 10/2020 | Bovay |
| 2020/0330167 A1 | 10/2020 | Romo |

FOREIGN PATENT DOCUMENTS

| | | |
|---|---|---|
| CN | 103298414 | 9/2013 |
| CN | 104619281 | 5/2015 |
| CN | 205729413 | 11/2016 |
| EP | 1 321 106 | 6/2003 |
| EP | 1 849 423 | 10/2007 |
| JP | 2005-270464 | 10/2005 |
| JP | 2006334149 A | 12/2006 |
| JP | 2015530149 A | 10/2015 |
| JP | 2016515847 A | 6/2016 |
| WO | 1991009375 A1 | 6/1991 |
| WO | 2008065600 A3 | 11/2009 |
| WO | 2009148317 A1 | 12/2009 |
| WO | 2008111070 A3 | 2/2010 |
| WO | WO 11/161218 | 12/2011 |
| WO | WO 13/107468 | 7/2013 |
| WO | WO 13/130895 | 9/2013 |
| WO | WO 15/153174 | 10/2015 |
| WO | WO 16/137612 | 9/2016 |
| WO | WO 17/114855 | 7/2017 |
| WO | WO 18/069679 | 4/2018 |
| WO | WO 18/189722 | 10/2018 |

OTHER PUBLICATIONS

Non-Final Rejection for U.S. Appl. No. 15/937,516, dated May 3, 2019, 13 pages.
Notice of Allowance for U.S. Appl. No. 15/937,516, dated Jul. 27, 2020, 2 pages.
Notice of Allowance for U.S. Appl. No. 15/937,516, dated Jun. 4, 2020, 7 pages.
International Search Report and Written Opinion dated Aug. 1, 2018 in application No. PCT/US18/24663.
JP Office Action for appl. no. 2019553015, dated Mar. 29, 2022, 6 pages.
Devin V. Amin et al., Ultrasound Registration of the Bone Surface for Surgical Navigation, Computer Aided Surgery, 8:1-16, 2003, 17 pages.
Heinz-Theo Luebbers et al., Comparison of different registration methods for surgical navigation in cranio-maxillofacial surgery, Journal of Cranio-Maxillofacial Surgery, 36:109-116, 2008, 8 pages.
Intuitive, System, Instruments, and Accessories User Manual, 91 pages.
Ion by Intuitive, available at https://www.intuitive.com/en-us/products-and-services/ion, last accessed Aug. 12, 2021, 6 pages.
Jeffrey H. Shuhaiber, Augmented Reality in Surgery, Archive of Surgery, 139:170-174, Feb. 2004, 5 pages.
Matthias Baumhauer et al., Navigation in Endoscopic Soft Tissue Surgery—Perspectives and Limitations, Journal of Endourology, 22(4):1-15, 2008, 16 pages.
MicroBIRD Product Brochure, Ascension Technology Corporation, available at http://www.ascension-tech.com/products/microbird.php, Jun. 12, 2019, 3 pages.
Robert Galloway & Terry Peters, Chapter 1: Overview and History of Image-Guided Interventions; David Holmes III et al, Chapter 3: Visualization in Image-Guided Interventions; Ziv Yaniv, Chapter 6: Rigid Registration, in Image-Guided Interventions: Technology and Applications, Terry Peters & Kevin Cleary eds., 2008, 95 pages.
Sargent, Dusty & Chen, Chao-I & Wang, Yuanfang, Cross Modality Registration of Video and Magnetic Tracker Data for 3D Appearance and Structure Modeling. Proceedings of SPIE—The International Society for Optical Engineering, 2010, 8 pages.
AU Examination Report for Appl. No. 2018244318, dated Mar. 9, 2023, 3 pages.
AU Examination Report for Appl. No. 2018244318, dated Nov. 10, 2022, 4 pages.
Notice of Preliminary Rejection for Appl. No. 1020187028149, dated Sep. 22, 2022, 11 pages.
AU Examination Report for Appl. No. 2018244318, dated Aug. 9, 2023, 3 pages.
Notice of Acceptance for Appl. No. 2018244318, dated Nov. 2, 2023, 3 pages.

* cited by examiner

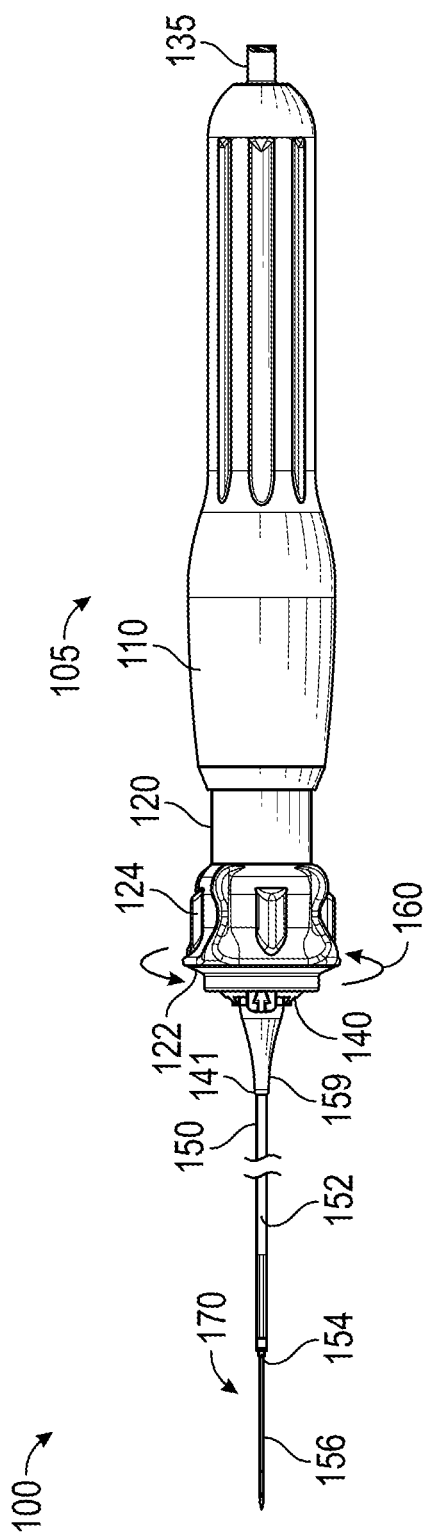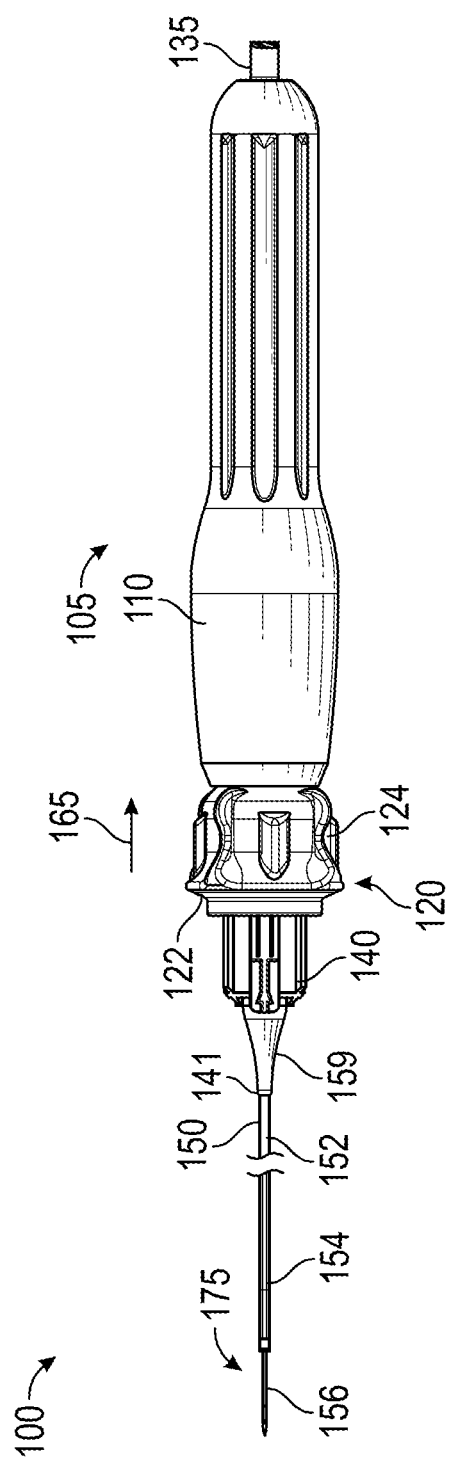
FIG. 1A
FIG. 1B

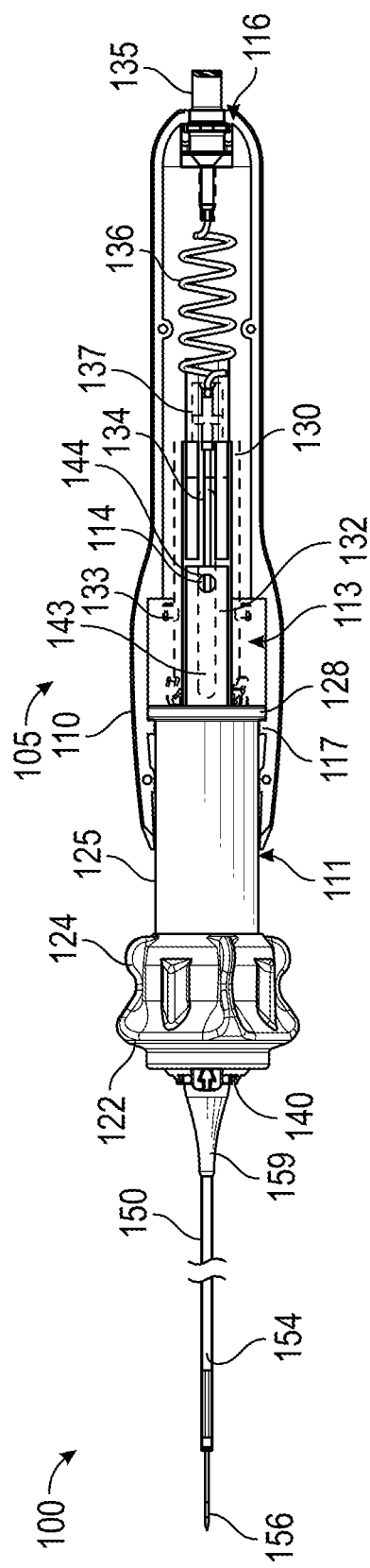
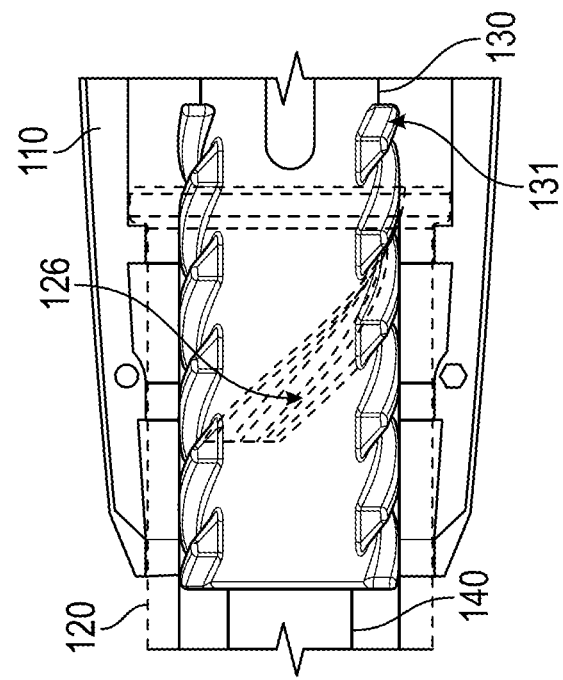
FIG. 1C
FIG. 1D

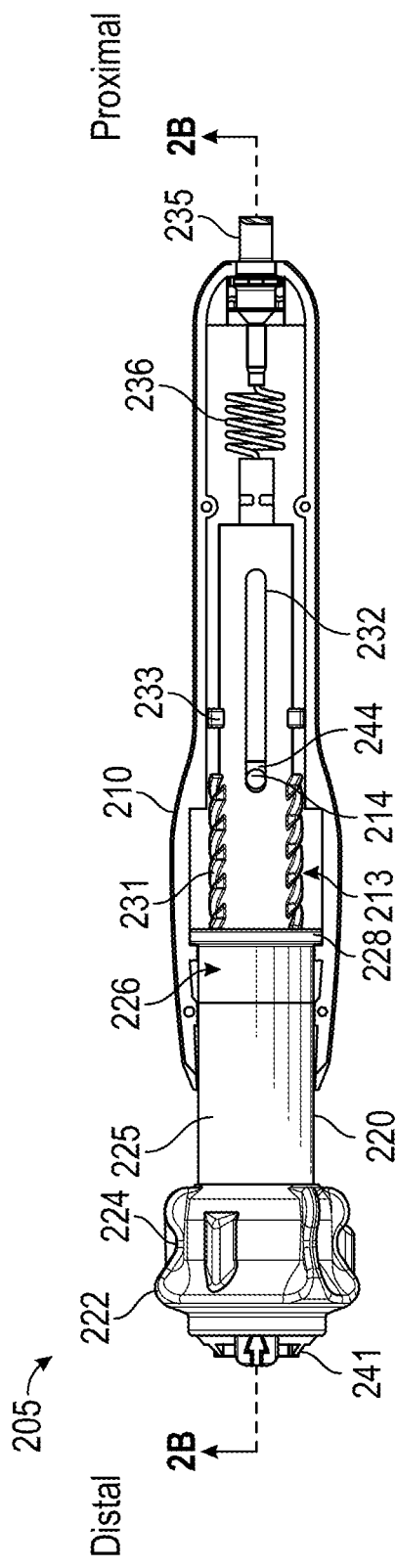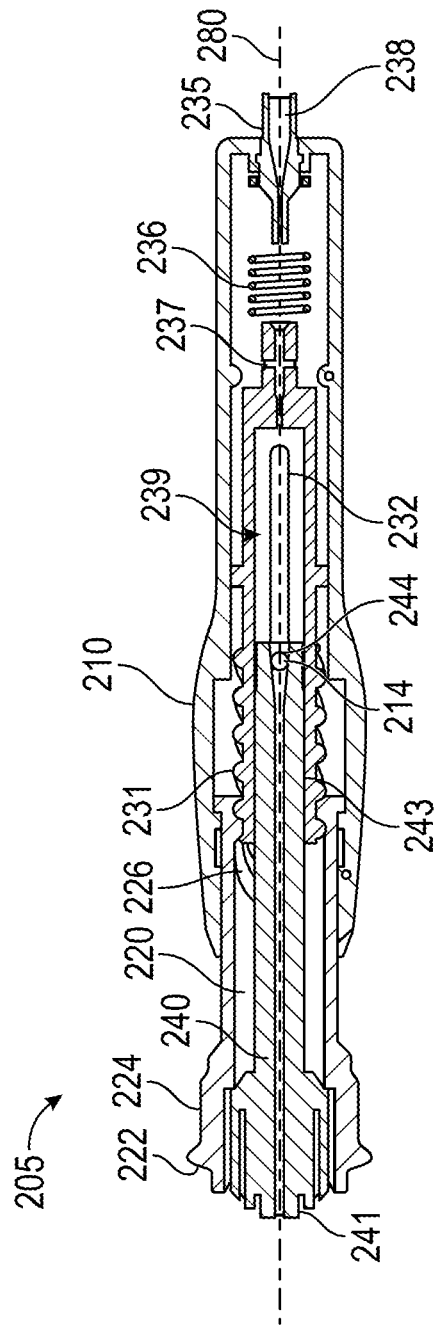
FIG. 2A
FIG. 2B

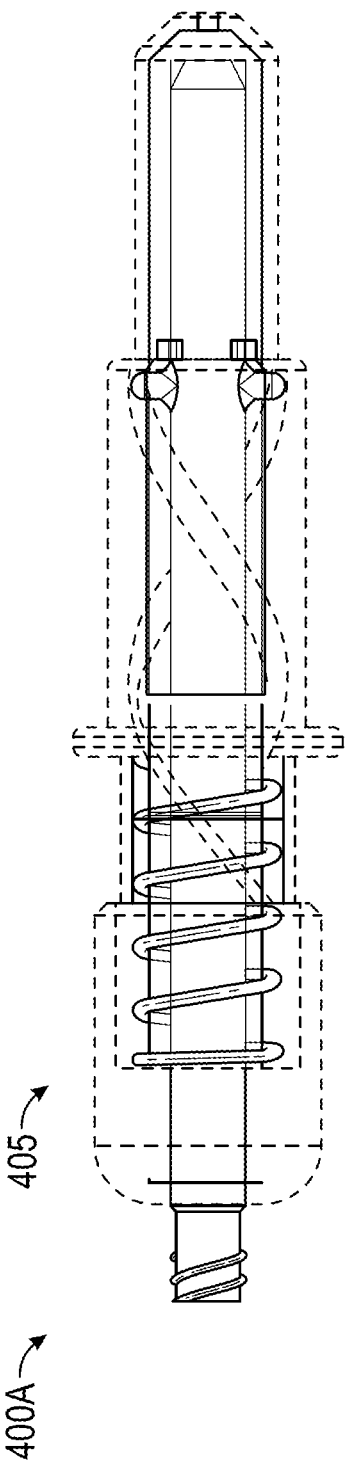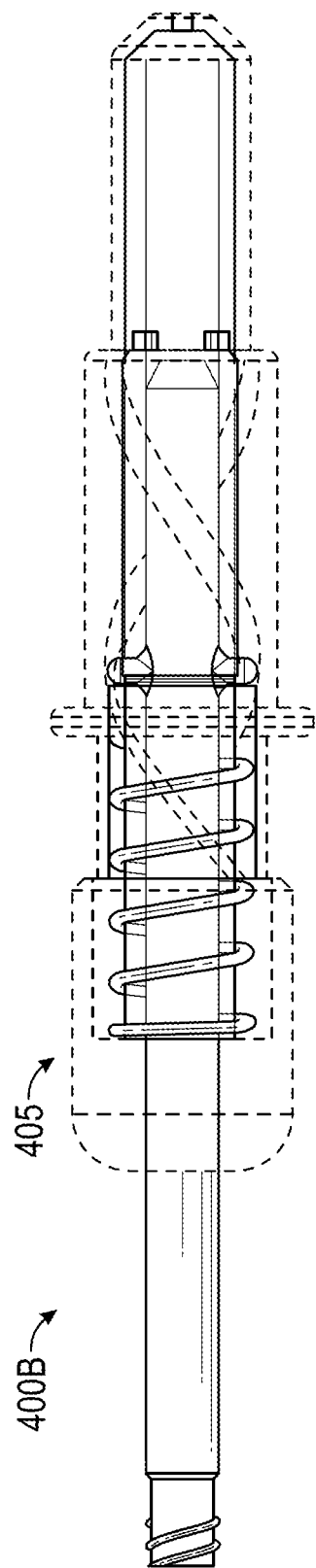
FIG. 4A
FIG. 4B

SHAFT ACTUATING HANDLE

CROSS-REFERENCE TO RELATED APPLICATION(S)

The present application is a continuation of U.S. patent application Ser. No. 15/937,516, filed Mar. 27, 2018, which claims the benefit under 35 U.S.C. § 119(e) of U.S. Provisional Patent Application No. 62/477,872, filed on Mar. 28, 2017, each of which is hereby incorporated by reference herein in its entirety.

TECHNICAL FIELD

The present disclosure relates generally to surgical devices, and more particularly to a handle for actuating extension and retraction of a remotely-disposed instrument via a shaft coupled between the handle and the instrument.

BACKGROUND

Endoscopy (e.g., bronchoscopy) may involve accessing and visualizing the inside of a patient's airways for diagnostic and/or therapeutic purposes. During a bronchoscopy procedure a flexible tubular tool, known as a bronchoscope, may be inserted into the patient's nose or mouth and passed down the patient's throat into the lung airways towards a tissue site identified for subsequent diagnosis and/or treatment. The bronchoscope can have an interior lumen (a "working channel") providing a pathway to the tissue site, and catheters and various medical tools can be inserted through the working channel to the tissue site.

SUMMARY

The systems, methods and devices of this disclosure each have several innovative aspects, no single one of which is solely responsible for the desirable attributes disclosed herein.

One aspect relates to a handle configured to drive movement of a bronchoscopy instrument, the handle extending along a longitudinal axis between a proximal end and a distal end of the handle and comprising a casing having an inner surface defining an internal volume including a spring housing portion; a proximal handle member positioned at least partly within a proximal portion of the internal volume of the casing and including a first helical cam interface, the proximal handle member configured to couple to a proximal end of an elongate channel extending beyond the distal end of the handle with a distal end of the elongate channel coupled to the bronchoscopy instrument; an actuation sleeve positioned at least partly within a distal portion of the internal volume of the casing and including a proximal portion having a second helical cam interface engaging the first helical cam interface, a rotation grip extending distally from the proximal portion of the actuation sleeve, and a plunger grip formed by a distal surface of the actuation sleeve; and a spring having a first end secured within the spring housing portion of the casing and a second end engaging the proximal portion of the actuation sleeve.

In some implementations, the spring is positioned to compress and expand along the longitudinal axis during movement of the actuation sleeve via the plunger.

In some implementations, the second helical cam interface engaging the first helical cam interface is configured to translate rotation of the rotation grip into linear motion of the proximal handle member along the longitudinal axis of the device, and wherein the linear motion of the proximal handle member is configured to drive the movement of the instrument via the elongate channel.

In some implementations, the second helical cam interface engaging the first helical cam interface translates proximal retraction of the plunger grip into proximal motion of the proximal handle member along the longitudinal axis of the device, and wherein the linear motion of the proximal handle member is configured to drive proximal retraction of the instrument via the elongate channel; and the spring is positioned to compress as the plunger grip is retracted proximally such that, upon release of the plunger grip, a bias of the spring drives distal linear motion of the proximal handle member along the longitudinal axis of the device, and wherein the linear motion of the proximal handle member is configured to drive distal extension of the instrument.

Some implementations further comprise a distal handle member positioned within the casing; and an internal receiving portion at a distal portion of the proximal handle member, wherein a proximal portion of the distal handle member is positioned within the internal receiving portion. Some implementations further comprise a lumen extending through the device along the longitudinal axis, wherein a distal portion of the lumen extends through the distal handle member and a proximal portion of the lumen extends through the proximal handle member. Some implementations further comprise a distal aperture formed in a distal end of the distal handle member, wherein the lumen is sized to accommodate positioning of the elongate channel within the lumen, and wherein the distal aperture is sized to accommodate passage of the elongate channel through the distal aperture. Some implementations further comprise a peg extending inwardly within the internal volume of the casing; an aperture in the distal handle member sized and positioned to receive the peg, wherein the distal handle member is fixed relative to the casing via the received peg; and an elongate slot formed in a wall of the proximal handle member, wherein the elongate slot is sized and positioned to slide around the peg with the wall of the proximal handle member positioned between the casing and the distal handle member.

Some implementations further comprise a fluid fitting at a proximal end of the proximal handle member, the fluid fitting configured to couple to an aspiration device or a respiration device. Some implementations further comprise a flexible shaft portion of the proximal handle member positioned between the second helical cam interface and the fluid fitting, wherein the fluid fitting is fixed relative to the casing. In some implementations, the flexible shaft portion comprises a length of coiled conduit. Some implementations further comprise a rigid shaft portion of proximal handle member extending between the second helical cam interface and the fluid fitting, wherein a proximal portion of rigid shaft portion is coupled to the fluid fitting, and wherein the rigid shaft portion is slidably engaged with a proximal aperture of the casing.

Some implementations further comprise a proximal flange of actuation sleeve and an internal flange positioned at a distal end of the spring housing portion, wherein the spring biases the proximal flange against the internal flange in its extended state.

Some implementations further comprise a support annulus of the proximal handle member sized to slidably engage a proximal portion of the internal volume of the casing.

Another aspect relates to a handle configured to drive movement of an instrument, the handle extending along a longitudinal axis between a proximal end and a distal end of the handle and comprising a casing having an inner surface defining an internal volume; a proximal handle member configured to couple to a channel extending beyond the distal end of the handle to the instrument; an actuation sleeve; a rotational motion transmitting interface coupling the proximal handle member to the actuation sleeve and configured to translate rotational motion of the actuation sleeve into linear motion of the proximal handle member along the longitudinal axis of the handle; and a plunging mechanism configured to drive distal movement of the proximal handle member along the longitudinal axis, the plunging mechanism comprising a biasing element positioned to compress and expand along the longitudinal axis during movement of the actuation sleeve.

In some implementations, expansion of the biasing element drives the distal movement of the proximal handle member along the longitudinal axis. In some implementations, the plunging mechanism comprises a grip of the actuation sleeve positioned such that pressure applied to the grip drives proximal movement of the actuation sleeve along the longitudinal axis and drives compression of the biasing element. In some implementations, the rotational motion transmitting interface coupling the proximal handle member to the actuation sleeve is configured to transmit the proximal and distal movement of the actuation sleeve to the proximal handle member. In some implementations, the biasing element comprises one of a spring, opposing magnets, hydraulic fluid, and a shape memory alloy.

Another aspect relates to an apparatus configured to drive movement of an instrument, the apparatus extending along a longitudinal axis between a proximal end and a distal end of the apparatus and comprising: a casing having an inner surface defining an internal volume; an actuation sleeve configured to impart linear motion along the longitudinal axis to the instrument and including a grip extending beyond a distal end of the casing; and a biasing element within the internal volume, the biasing element positioned to compress and expand along the longitudinal axis during movement of the actuation sleeve wherein expansion of the biasing element drives linear movement of the actuation sleeve in a proximal direction along the longitudinal axis.

In some implementations, the grip is positioned such that pressure applied to the grip drives the linear movement of the actuation sleeve along the longitudinal axis and drives compression of the biasing element.

Some implementations further comprise a proximal handle member; and a rotational motion transmitting interface coupling the proximal handle member to the actuation sleeve and configured to translate rotational motion of the actuation sleeve into linear motion of the proximal handle member along the longitudinal axis of the handle, wherein the rotational motion transmitting interface coupling the proximal handle member to the actuation sleeve is further configured to transmit the linear movement of the actuation sleeve to the proximal handle member. Some implementations further comprise a distal handle member positioned at least partly within the actuation sleeve and comprising a rounded protrusion, wherein the actuation sleeve comprises at least one detent positioned to engage the rounded protrusion during rotation of the actuation sleeve. Some implementations further comprise a lock to fix relative positioning of the actuation sleeve and the proximal handle member prior to actuating linear movement of the actuation sleeve.

In some implementations, the biasing element comprises one of a spring, opposing magnets, hydraulic fluid, and a shape memory alloy.

Another aspect relates to a method of accessing a target tissue site of a patient with an instrument, the method comprising actuating a first motion transmitting interface of a delivery handle coupled to the instrument, wherein actuating the first motion transmitting interface causes a distal end of the instrument to advance through a working channel of a bronchoscope inserted at least partly into the patient; determining that the distal end of the instrument is positioned within the target tissue site; and actuating a second motion transmitting interface of the delivery handle, wherein actuating the second motion transmitting interface causes extension and retraction of the distal end of the instrument, by at least applying a pressure to a portion of the delivery handle to compress a biasing element of the second motion transmitting interface, and drive retracting motion of the instrument to withdraw the distal end of the instrument from the tissue site, and releasing at least some of the pressure from the portion of the delivery handle to allow expansion of the second motion transmitting interface, wherein the expansion of the biasing element drives the distal end of the instrument into the tissue site.

In some implementations, actuating the first motion transmitting mechanism and actuating the second motion transmitting mechanism are performed by a single hand of a user of the delivery handle.

In some implementations, releasing the expansion of the biasing element drives the distal end of the instrument up to approximately 2 cm.

In some implementations, releasing the expansion of the biasing element drives the distal end of the instrument up to an extension length of the distal end.

Some implementations further comprise configuring the delivery handle to provide a structural limit on a distance the biasing element drives the distal end of the instrument prior to actuating the second motion transmitting interface.

In some implementations, actuating the first motion transmitting interface causes the distal end of the instrument to extend up to approximately 3 cm beyond a distal end of the working channel.

In some implementations, actuating the first motion transmitting interface and actuating the second motion transmitting interface are performed by a robotic control system.

Another aspect relates to a robotic system, comprising an instrument, comprising a tool coupled to a distal end of a shaft; and a handle extending along a longitudinal axis and configured to drive movement of the tool with the shaft extending through a distal end of the handle, the handle comprising a member configured to move along the longitudinal axis, wherein a proximal end of the shaft is coupled to the movable member, an actuation sleeve having at least one grip portion, a motion transmitting interface coupling the member to the actuation sleeve and configured to translate rotational motion of the actuation sleeve into motion of the member along the longitudinal axis, and a biasing element positioned to compress and expand along the longitudinal axis of the handle in response to a plunging motion of the actuation sleeve driven by application and release of pressure on the at least one grip portion, wherein the motion transmitting interface is configured to translate the plunging motion of the actuation sleeve into motion of the member along the longitudinal axis; and a controller coupled to the actuation sleeve and configured to actuate the rotational motion and the plunging motion of the actuation sleeve.

In some implementations, the controller comprises at least one computer-readable memory having stored thereon executable instructions; and one or more processors in communication with the at least one computer-readable memory and configured to execute the instructions to cause the system to at least actuate the rotational motion and the plunging motion. In some implementations, the controller comprises an input device configured to receive control signals from a user, and wherein the one or more processors are configured to execute the instructions to cause the system to at least actuate the rotational motion and the plunging motion responsive to the control signals.

In some implementations, the instrument comprises a jacket coupled to the distal end of the handle and positioned around the shaft. In some implementations, the handle is configured to drive movement of the tool relative to the jacket.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIGS. 1A-1F illustrate an embodiment of a medical instrument including a shaft manipulating handle as described herein.

FIGS. 2A-2D illustrate another embodiment of a shaft manipulating handle as described herein.

FIGS. 4A-4H illustrate another embodiment of a shaft manipulating handle as described herein.

DETAILED DESCRIPTION

Introduction

Figure 1E:
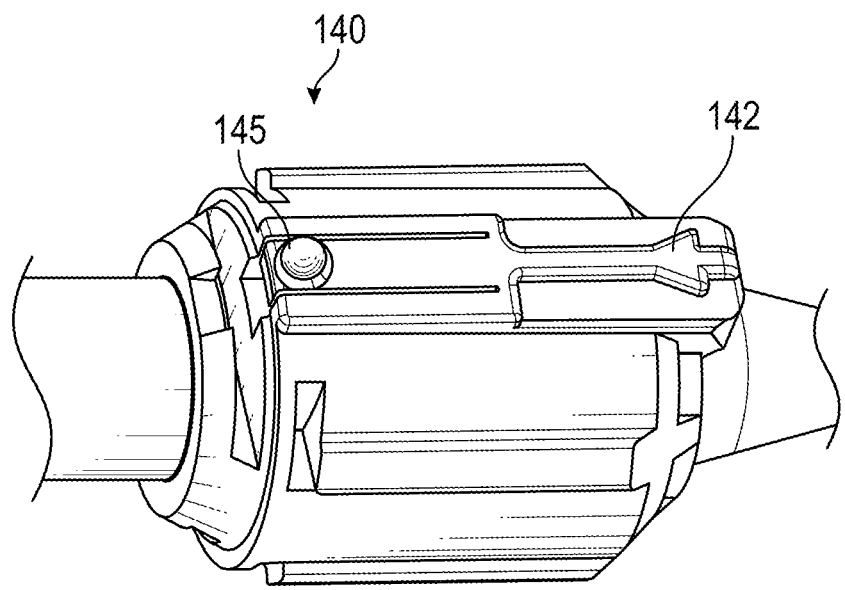

Medical procedures may involve manipulation of a tool positioned remotely from the operator, for example positioned through a channel inserted into the body of a patient. Such channels include trocars, catheters, and endoscopes including bronchoscopes. As one example of such a medical procedure, transbronchial needle aspiration (TBNA) can be used as a minimally invasive bronchoscopic technique for diagnosis and staging of bronchial diseases, including lung cancer. A TBNA technique can involve manipulating a biopsy needle through a flexible bronchoscope. For example, a physician can use chest scans to identify the location of a mass to be biopsied and to guide positioning of the bronchoscope within the patient's airways towards that mass. After the distal end of the bronchoscope working channel is positioned within the airways near the identified mass, an elongate, tubular jacket containing the biopsy needle can be advanced through the working channel to the sampling area. The target tissue can then be pierced by extending the needle out of the jacket, and aspiration can be applied to aid sample acquisition. Typically, aspiration involves holding the proximal end of a tube attached to the needle by hand and manually moving the tube backward and forward relative to the bronchoscope to repeatedly puncture the tissue site with the needle. After sample acquisition, the needle can be retracted back into the sheath and withdrawn through the working channel. In some procedures, sample analysis can be performed in the same room as the TBNA procedure, and depending upon results of the analysis further TBNA sample acquisition and/or other tissue sampling or treatment can be performed.

However, bronchoscopy techniques including TBNA can have difficulty accessing masses at the periphery of the lungs, particularly if such masses are still relatively small, for example around 8 mm or smaller. This limitation can prevent successful use of bronchoscopy in diagnosing and staging cancerous masses in early stages, a timeframe during which such masses may be more easily treatable and may not have spread to other places in the patient's body. Another consideration with bronchoscopy at the lung periphery relates to the risk of pneumothorax if the needle (or other tool) is not carefully controlled and thus pierces the lung. Further, existing bronchoscopy systems usable for TBNA and other airway sampling and treatment techniques require multi-handed operation, often involving multiple people to position and maintain the bronchoscope and then to actuate movement of instruments through the bronchoscope working channel.

The aforementioned problems, among others, are addressed in some embodiments by the actuating handles described herein. Embodiments of the disclosure relate to actuating handles, specifically handles for actuating extension and retraction of a medical tool disposed remotely from the handle via a shaft coupled between the handle and the tool. Further, the described handles provide multiple modalities for moving such tools. The handle can include mechanisms that permit control of linear motion of the shaft secured within the handle, for example including one or both of a rotational interface and a plunging interface. The rotational interface can allow for fine-control positioning of the shaft, for example by allowing a user to rotate the rotational interface to extend or retract the shaft. Some implementations of the rotational interface can include detents to provide physical feedback (e.g., haptic feedback) to the user regarding when the rotation has caused a certain interval of the extension or retraction. The plunging interface can enable a faster linear motion, for example by implementing a biasing mechanism such as a spring that compresses during retraction of the shaft and then releases to drive rapid linear motion in the extension direction.

Thus, the disclosed handle can provide enhanced control of the medical tool through the multiple motion-transmitting interfaces, and can be sized such that both interfaces are capable of use by a single hand. Beneficially, this can allow a physician to actuate tool motion themselves during an endoscopic procedure without requiring another person to assist.

In the context of use with a bronchial tool, the rotational interface can be structured to provide sufficient extension of the tool to reach the lung periphery from the distal end of the working channel, thus improving access to previously inaccessible masses peripheral lung regions. Further in the context of use with a bronchial tool, the rotational interface can be structured to only allow extension of the tool tip by a specified amount that is equal to or slightly smaller than (e.g., several millimeters) the expected distance between the working channel distal end and the outer edge of the lung. For example, some bronchoscope systems can position the working channel distal end approximately 2.5 cm to 3 cm from the outer edge of the lung. Thus, a handle designed for use with such a system can limit needle extension to 2.5 cm or 3 cm in order to enable biopsy of a mass at the lung periphery while reducing the risk of pneumothorax. It will be appreciated that this specific distance is provided for example only, and that different handles according to the present disclosure can be made to provide specific extension distances corresponding to specific bronchoscopes. Further, the plunging interface can beneficially be designed in such embodiments to withdraw the needle or tool from the tissue site so that the maximum extension distance of the rotational interface is not exceeded. Releasing the tool back into the tissue site with force via the biasing element of the plunging interface can beneficially aid in collection of tissue samples in some embodiments.

A handle, according to the present disclosure, can be provided for an elongate medical instrument designed to be operated through a working channel positioned in a body cavity of a patient. The medical instrument can have an elongate shaft, tube, or wire coupled to a tool. For example, the instrument can be a flexible sheath containing biopsy needle coupled to a distal end of a tube, with the needle positioned at a distal end of the flexible sheath. Additional examples of tools that can be used with the disclosed handles include brushes (e.g., a cytology brushes), needle-tipped cytology brushes, forceps (e.g. biopsy forceps), baskets, bone biopsy needles, fiducial markers and their delivery mechanisms, diathermy snares, laproscopic tools, angioplasty balloons, stents, or other endoscopic or catheter-delivered or catheter-based medical instruments or tools.

As used herein, "distal" refers to the end of the scope or tool positioned closest to the patient tissue site during use, and "proximal" refers to the end of the sheath or tool positioned closest to the operator (e.g., a physician or a robotic control system). Stated differently, the relative positions of components of the sheath, tool, and/or the robotic system are described herein from the vantage point of the operator.

Thus, as used herein, a "remotely-disposed" tool refers to the tool being located at or beyond the distal end of a working channel with the handle being located at or beyond the proximal end of the working channel. The term remotely-disposed can also refer to tools that are not inserted through any working channel but are separated from the handle by a distance spanning an elongate jacket containing the tool, for example a catheter positioned through a blood vessel or other luminous passage of a patient.

As used herein, a biasing element can be one or more of a spring, opposing magnets, hydraulic systems, compressible shape memory alloys, and other mechanisms that can store potential energy in compression or extension and then effect movement due to release of the potential energy during the other of extension or compression.

As used herein, the term "dithering" refers to a back and forth motion of a medical instrument such as a biopsy needle, for example by extension and retraction of the instrument using the plunging interface of the handle described herein. In some cases, the back and forth motion of the medical instrument occurs independent of the movement of the instrument's jacket such that the jacket of the medical instrument remains relatively stationary during the dithering.

The disclosed systems and techniques can provide advantages for bronchoscopic needle biopsies and other applications, including manipulation of other endoscopic, laparoscopic, and/or catheter-delivered tools. Thus, though the disclosed handles are described in many portions of the present disclosure within the context of bronchoscopy biopsy needles, it should be understood that such handles can also be used with other remotely-disposed tools in order to provide the disclosed benefits. Further, though the disclosed handle is illustrated and described with both the plunging and rotational interfaces, it will be appreciated that alternatives can include one of these interfaces without the other, and that the plunging features from the various embodiments described herein can be combined with the rotational features from other embodiments described herein.

Robotic surgical systems can utilize endoscopic instruments to perform minimally invasive endoscopic procedures robotically. Thus, some implementations of the disclosure relate to surgical instruments and systems that include shaft actuation handles that can advantageously be used in robotically-guided (whether fully automated robotic systems or robotic systems that provide some level of assistance) medical procedures, and methods of performing a medical procedure under guidance of a robotic surgical system. In such systems, a robotic arm can be configured to control the rotation and plunging motions described herein. Drive signals for such actuation can be supplied by the robotic surgical system, for example in response to user input via an input device and/or computer-controlled surgical processes.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Overview of Example Handles

Figure 1F:
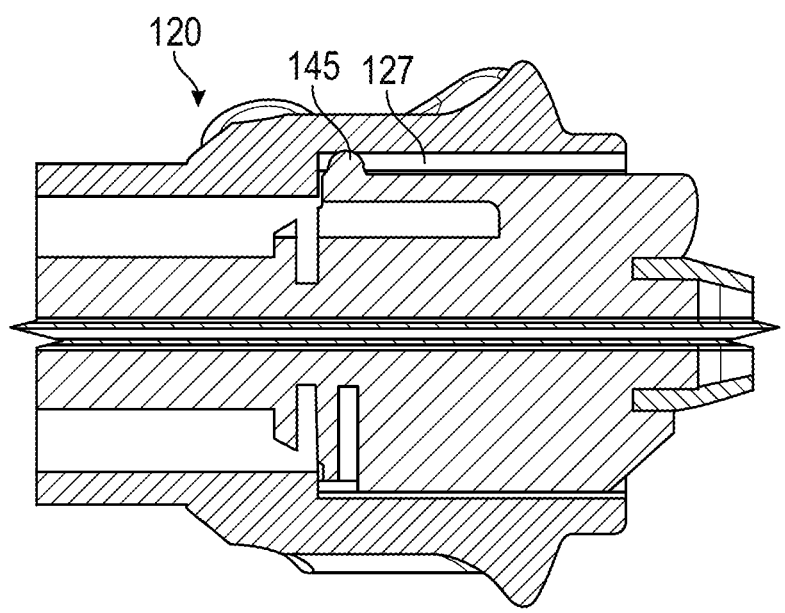

FIGS. 1A-1F illustrate an embodiment of a medical instrument 100 including a shaft manipulating handle 105, jacket 150, conduit 154, and tool 156. FIG. 1A illustrates an outer view of the instrument 100 and the rotational 160 modality. FIG. 1B illustrates an outer view of the instrument 100 and the plunging 165 modality. FIG. 1C illustrates a cutaway view of the handle 105 of the instrument 100. FIG. 1D illustrates a cutaway view of a portion of the handle 105 with the actuation sleeve 120 shown with reduced opacity to reveal interior structures. FIG. 1E illustrates an outer view of the distal handle member 140, and FIG. 1F illustrates a cross-sectional view of the distal handle member 140 within the actuation sleeve 120. FIGS. 1A-1F are discussed together in portions of the description below due to the overlap of depicted features.

With reference to FIG. 1A, the handle 105 includes an actuation sleeve 120, distal handle member 140, casing 110, and fluid fitting 135. The actuation sleeve 120 includes a rotational wheel grip 124 and a plunger grip 122. As shown in FIG. 1A, an operator can drive motion of the tool 156 relative to the jacket 150 by rotating 160 the rotational wheel grip 124, which causes rotation of the actuation sleeve 120 around the longitudinal axis of the handle 105. Rotation 160 in one direction can cause extension of the tool 156 from the jacket 150. Rotation in the other direction can retract the tool 156 back into the jacket 150. The internal components of the handle 105 that transfer this motion to the tool 156 are described in more detail below. As described in more detail below, the components of the handle 105 can be structured to provide physical feedback to the user at predetermined intervals to assist in fine control of the tool extension.

The plunging modality, as illustrated in FIG. 1B, can be driven in one direction by an application of force by the operator to plunger grip 122 and driven in the opposite direction by a biasing element upon release of the force. The biasing element and internal components of the handle the handle 105 that transfer this motion to the tool 156 are discussed in more detail below. When the actuation sleeve 120 is drawn proximally as shown by arrow 165 in FIG. 1B, for example by application of pressure to the plunging surface 122, the biasing element can be compressed. Upon release of at least some of the pressure from the plunging grip 122 the biasing element can expand, thereby driving distal motion of the actuation sleeve 120. In the embodiment of FIGS. 1A and 1B, during rotation 160 and plunging 165 the fluid fitting 135 may remain stationary with respect to the casing 110 of the handle.

Due to the biasing element, the plunging modality can be useful for effecting a dithering motion of the tool. For example, the tool can be extended to a desired maximum distance using the rotational modality, such as a desired distance into patient tissue. By applying pressure to the plunging grip 122, an operator can retract the actuation sleeve, thereby driving retraction of the tool proximally towards the operator and away from the patient tissue. In some embodiments, complete retraction of the actuation sleeve 120 can retract the tool by approximately 1.5 cm, approximately 2 cm, or another desired distance. Thus, the plunging motion may not cause further extension of the tool. This can be beneficial during use in pulmonary procedures near the lung periphery to mitigate the risk of pneumothorax. Dithering of a tool such as a biopsy needle, which refers to the repeated retraction and extension as can be caused by multiple uses of the plunging modality, can assist in acquisition of a suitable tissue sample.

The jacket 150, conduit 154, and tool 156 of the medical instrument are illustrated together with the handle 105 in FIGS. 1A-1C. As illustrated, the jacket 150 extends from a distal aperture 141 of the handle 105 through strain relief 159, and can contain some or all of the conduit 154 and tool 156 in various configurations. The tool 156 is depicted as a needle and the conduit 154 has an interior lumen 152 that provides at least a portion of a fluid pathway between a proximal aperture of the fluid coupling 135 of the handle 105 and the distal end of the tool 156. The tool 156 can be a biopsy needle such as an aspiration needle configured for acquisition of tissue samples or can be configured for delivery of therapeutic agents to a tissue site. In other examples, the tool 156 can be a brush (e.g., a cytology brush), a needle-tipped cytology brush, forceps (e.g. biopsy forceps), or other tools as described above. Where aspiration is not required with a particular tool, the conduit may have no interior lumen and instead may have a solid cross-section or be composed of braided strands.

The views of FIGS. 1C and 1D show internal components of the handle 105. As shown in FIG. 1C, the handle 105 includes a casing 110, actuation sleeve 120, proximal handle member 130, and distal handle member 140. These components can be printed, molded, or machined from suitable materials including plastics, metals, and composites. Extending from a distal aperture 141 of the handle 105 is a flexible, tubular jacket 150. A strain relief 159 may be fitted with the distal end of the handle 105 around the jacket 150. A conduit 154 is positioned within the interior lumen of the jacket 150 and coupled to a medical tool 156 at its distal end and to the proximal handle member 130 at its proximal end. As such, linear motion of the proximal handle member 130 along a longitudinal axis of the handle 105 via one or both of the rotational and plunging modalities described herein can drive corresponding motion of the conduit 154, thus driving extension and retraction of the tool relative to the distal end of the jacket 150.

The casing 110 can provide an internal volume to enclose at least a portion of the moving parts of the handle 105, and can provide an external surface sized and shaped to provide a comfortable surface for grasping with a single hand in some implementations. For example, a user can hold a portion of the casing 110 in the palm and heel of the hand while manipulating the actuation sleeve 120 with the fingers, thereby allowing the user to control extension and retraction of the tool 156 with a single hand. The casing 110 can include a distal aperture 111 at its distal end and a proximal aperture 116 at its proximal end.

A portion of the internal volume of the casing can provide a housing 113 for constraining the range of motion of the actuation sleeve 120. This housing 113 can have a larger diameter than a distal portion of the internal volume in some embodiments in order to provide an annular surface for engaging the flange 128 of the actuation sleeve at a fully retracted position of the actuation sleeve 120. The flange 128 of the actuation sleeve can abut a flange 117 of the casing 110 at a fully extended position. The flange 117 can serve to limit the extension of the actuation sleeve 120 relative to the casing 110. Thus, in some embodiments the length of the housing 113 can be selected to correspond to the desired range of motion of the actuation sleeve 120. In some embodiments the positioning of flange 117 along the longitudinal axis of the handle 105 may not be fixed, and an operator can adjust its positioning to provide control over the desired plunging distance.

The housing 113 can additionally contain a spring or other biasing element, for example a pair of opposing magnets, a chamber of compressible hydraulic fluid, or a shape memory alloy. The annular proximal surface of the housing 113 can engage a proximal portion of the biasing element, and a distal portion of the biasing element can engage the flange 128 of the actuation sleeve 120. In some embodiments, when the actuation sleeve 120 is drawn proximally as shown by arrow 165 in FIG. 1B, the biasing element can be compressed by proximal movement of the flange 128 of the actuation sleeve 120. Upon release of the pressure on the plunging grip the biasing element will expand and drive the actuation sleeve 120 distally until flange 128 abuts flange 117 of casing 110, thereby driving the tool back to its extended position.

Figure 3A:
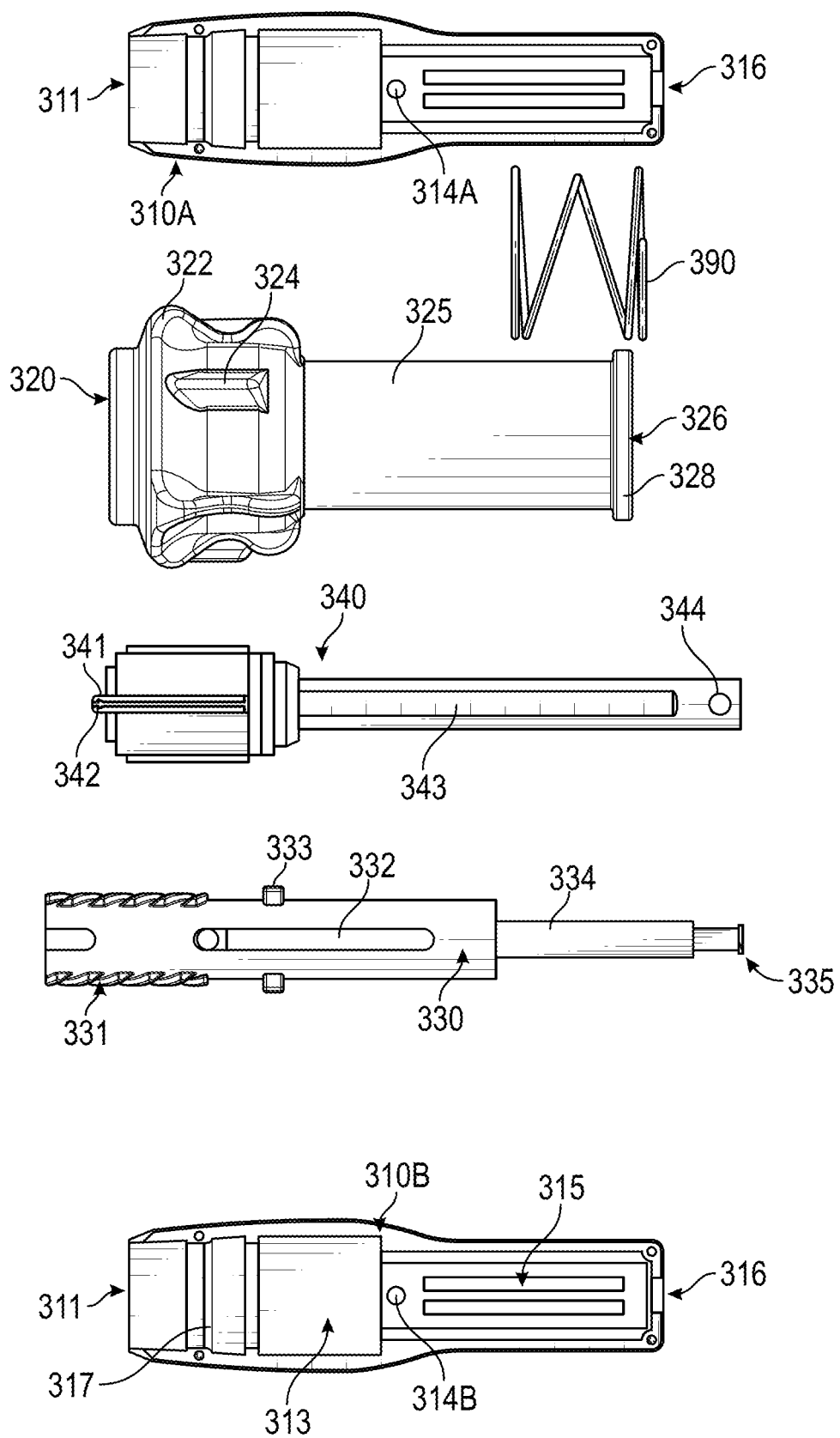
FIGS. 3A and 3B illustrate photos of an example shaft manipulating handle as described herein.

The casing 110 can also include at least one prong 114 positioned to extend into the aperture 144 of the distal handle member 140 to secure the distal handle member 140 relative to the casing 110. The prong extending of the portion of casing 110 shown in FIG. 1C is positioned behind the conduit 154, and for reference a similar prong 314A, 314B are shown in FIG. 3A. The prong 114 can have a length sufficient to be secured within the aperture 144 of the distal handle member 140 without occluding the lumen through which conduit 154 passes. As such, the prong 114 can have a length of less than half the diameter of the internal volume of the casing 110.

The actuation sleeve 120 can have a proximal flange 128, a cylindrical body 125 extending from the flange 128 to a rotational wheel grip 124, plunger grip 122, and an internal cam interface (shown and described in actuation sleeve FIG. 1D). Rotational wheel grip 124 can be used to facilitate the rotational modality described and the plunger grip 122 can be used to facilitate the plunging modality as described above. For example, rotational wheel grip 124 can provide a number of grip surfaces extending radially from the distal end of the actuation sleeve. Plunger grip 122 can provide a surface that allows a user to exert force on a portion of the actuation sleeve 120 to draw actuation sleeve 120 proximally, and can be formed for example by a distal surface of the rotational wheel. The cylindrical body 125 can be sized to slide through the distal aperture 111 of the casing 110 during manipulation of the actuation sleeve 120 within the casing 110, and the flange 128 can abut the flange 117 of the casing 110 to provide a mechanical stop for forward extension of the actuation sleeve 120.

The proximal handle member 130 can include, from its proximal end towards its distal end: fluid fitting 135, proximal portion 136, recess 137, elongate slot 132, support annulus 133, and external cam interface 131. A portion of the external cam interface 131 is visible in FIG. 1C, and its interaction with an internal cam interface. An internal cam interface and the interaction between the external cam interface 131 and the internal cam interface is discussed in more detail below with respect to FIG. 1D.

The conduit 154 attached to tool 156 can be secured within recess 137, for example by bonding via an adhesive. Thus, linear motion of the proximal handle member 130 can transfer to the tool 156 via the conduit 154, allowing manipulation of the handle 105 to drive extension and retraction of tool 156 from jacket 150. In some embodiments the recess 137 can be structured to mechanically mate with a corresponding feature on the conduit 154 to facilitate use of the handle 105 with a number of different conduits and tools. Thus, in some embodiments the handle 105 may be sterilizable and reusable while the conduit, tool, and jacket may be disposable. In various other embodiments the entire instrument 100 may be entirely sterilizable and reusable or designed as a disposable single unit.

Fluid fitting 135 can be a threaded connector for securing to a corresponding threaded connector of an aspiration device, a respiration device, or device containing therapeutic agents. In one example, the fluid fitting 135 can be a Luer lock. The fluid fitting 135 can be secured within the proximal aperture 116 of the casing 110 in some embodiments. Securing the fluid fitting 135 to the casing 110 can provide benefits in terms of stability of the aspiration device when secured to the fluid fitting 135.

As shown, the proximal portion 136 of proximal handle member 130 can comprise a length of coiled tubing in some implementations having the fluid fitting 135 fixed to the casing 110. This can provide a flexible fluid path that accommodates linear motion of the proximal handle member 130. For example, the proximal portion 136 can be coiled HDPE tubing, and, in some embodiments, this can be a portion of the conduit 154 positioned proximally from the bonding recess 137. A sleeve of polyolefin heat shrink can be used to secure the coiled tubing to the fluid fitting in some implementations.

Elongate slot 132 can have a length and width sufficient to allow the prong of the casing 110 that secures the distal handle member 140 to slide through the slot 132 as the proximal handle member 130 moves linearly within the casing 110. Support annulus 133 can have an outer diameter that substantially matches the inner diameter of a proximal portion of the interior volume of the casing 110 to slidably engage the inner wall of the casing and provide stability to the proximal handle member 130 during linear movement.

The distal handle member 140 can have a proximal shaft 143 positioned partially within the actuation sleeve 120 and partially within the proximal handle member 130. The proximal shaft 143 can have a recess or aperture 144 sized to accept the prong 114 of the casing 110, thereby fixing the position of the distal handle member relative to the casing 110.

Turning specifically to FIG. 1D, an internal cam interface 126 of the actuation sleeve 120 can be formed as grooves extending in a helical or spiral structure around the inner surface of the actuation sleeve 120, and external cam interface 131 can be formed as ridges extending in a helical or spiral structure around the exterior surface of the proximal handle member 130. In other embodiments the internal cam interface 126 can comprise ridges and the external cam interface 131 can comprise grooves. The external cam interface 131 can be positioned at least partly within the actuation sleeve 120. The external cam interface 131 can engage the internal cam interface 126 of the actuation sleeve 120 to form a motion transmitting interface for transmitting rotational or linear motion of the actuation sleeve 120 to the proximal handle member 130. Thus, in embodiments where the internal cam interface 126 comprises grooves, the external cam interface 131 can comprise ridges angled to engage the grooves. Similarly, in embodiments where the internal cam interface 126 comprises ridges, the external cam interface 131 can comprise grooves angled to be engaged by the ridges.

The engaged external and internal cam interfaces 131, 126 shown in FIG. 1D can transfer the rotational motion of the actuation sleeve 120 to linear motion of the proximal handle member 130. The engaged external and internal cam interfaces 131, 126 can transfer the linear plunging motion of the actuation sleeve 120 to the proximal handle member 130 and thus to the conduit 154 and tool 156 shown in FIGS. 1A-1C. Although not illustrated, some embodiments may provide a lock for the actuation sleeve 120 to prevent further rotation during the plunging modality. The bond between the conduit 154 and the proximal handle member 130 can, in turn, transfer this motion to the tool to drive the extension and/or retraction.

As shown in FIGS. 1E and 1F, the distal end of the distal handle member 140 can include a position indicator 142 and a rounded protrusion 145. The position indicator 142 can line up with extension distance markings on a distal surface of the actuation sleeve 120 (see FIG. 2C and associated description for an example) in order to provide an operator with a visual indication of how far the tool is extending from the jacket 150 based on the rotation of the actuation sleeve 120.

The rounded protrusion 145 can be sized to allow rotation of the actuation sleeve 120 around the rounded protrusion 145 while slightly compressing the rounded protrusion 145 inwardly into the distal handle member 140. The actuation sleeve 120 can have one or more detents 127 sized to receive the uncompressed rounded protrusion 145 to provide physical feedback to an operator when the actuation sleeve 120 has been rotated a specified amount and to gently lock the position of the actuation sleeve 120 relative to the distal handle member 140. The actuation sleeve 120 can include a number of such detents aligned with distance markings visible to the user. For example, the actuation sleeve 120 can provide a detent and marking at intervals corresponding to every 1, 2, 5, or 10 mm of extension or retraction of the tool. One example can be configured to provide up to 30 mm of extension and can have a detent corresponding to every 5 mm of extension.

Figure 2C:
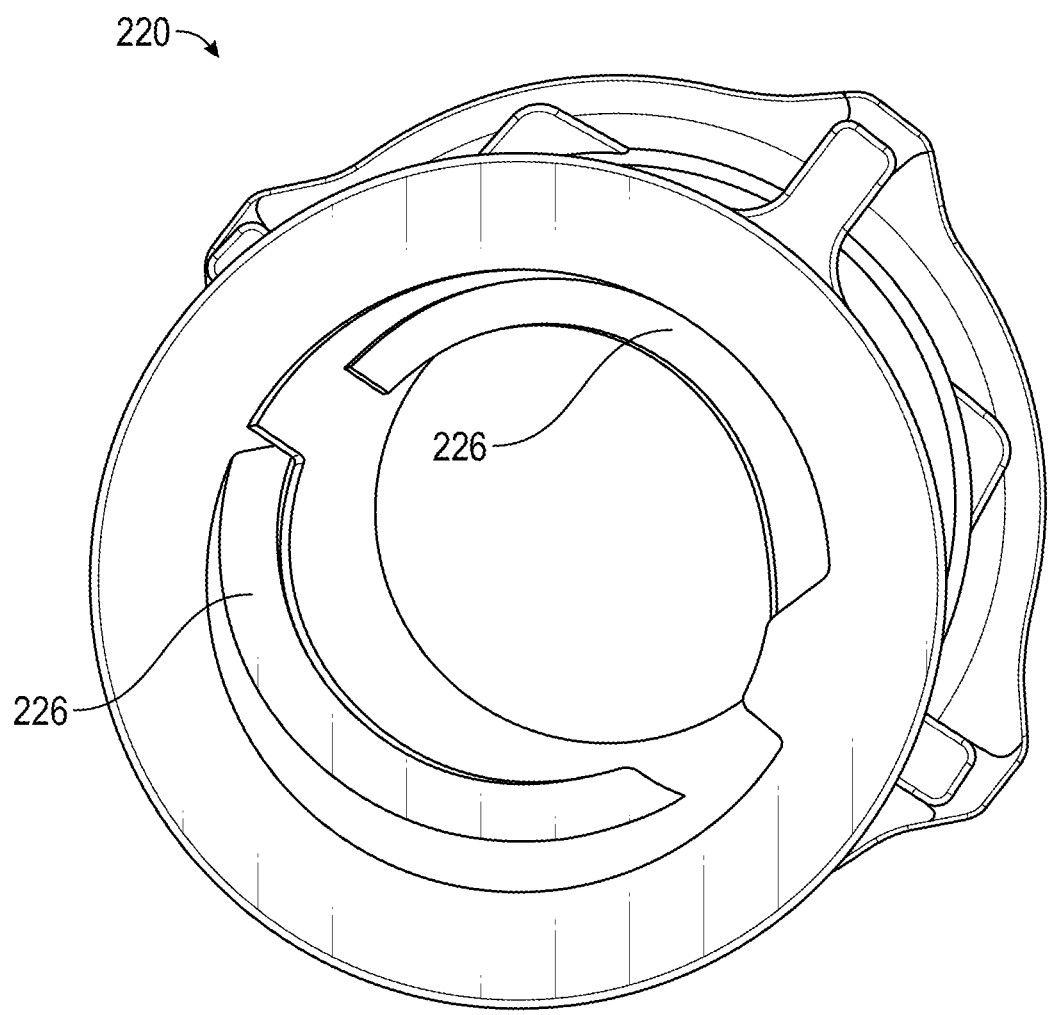
Figure 2D:
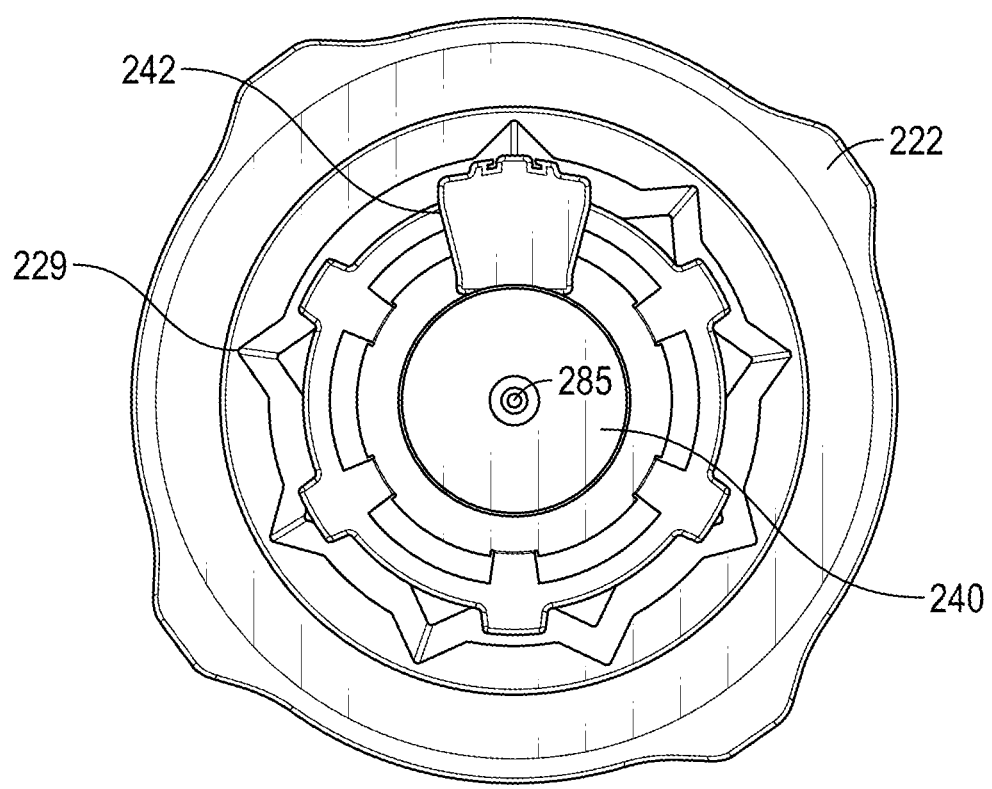

FIGS. 2A-2D illustrate another embodiment of a shaft manipulating handle 205 as described herein. FIG. 2A illustrates a cutaway view of the casing 210 of the handle 205 to reveal the actuation sleeve 120 and proximal handle member 230 within, with the actuation sleeve 120 shown with a slight opacity reduction to reveal the internal cam interface 228. FIG. 2B illustrates a cross-sectional view of the handle 205. FIG. 2C illustrates a perspective view of the actuation sleeve 220 of the handle 205. FIGS. 2A-2D will be discussed together below. FIG. 2D illustrates a front view of the handle.

Similar to the handle 105 of FIGS. 1A-1F, the handle 205 can be operated in both rotational and plunging modalities for fine tool driving and dithering. As shown in FIGS. 2A-2C, the handle 205 includes a casing 210, actuation sleeve 220, proximal handle member 230, and distal handle member 240 positioned along a longitudinal axis 280. A lumen 285 (shown in FIG. 2D) can form a fluid pathway from the proximal end of the handle 205 to the distal end of the handle 205.

The casing 210 can provide an internal volume to enclose at least a portion of the moving parts of the handle 205, and can provide an external surface sized and shaped to provide a comfortable surface for grasping with a single hand in some implementations. The casing 210 can include a distal aperture at its distal end and a proximal aperture at its proximal end. The casing 210 can also include at least one prong 214 positioned to extend into the aperture 244 of the distal handle member 240 without occluding the handle lumen 285 in order to secure the distal handle member 240 relative to the casing 210. A portion of the internal volume of the casing can provide a housing 213 for constraining the range of motion of the actuation sleeve 220 and housing a biasing element.

Similar to actuation sleeve 120, actuation sleeve 220 can have a proximal flange 228, a cylindrical body 225 extending from the flange 228 to a rotational wheel grip 224, plunger grip 222, and an internal cam interface 226. Rotational wheel grip 224 can be used to facilitate the rotational modality described herein, and the plunger grip 222 can be used to facilitate the plunging modality described herein. FIG. 2C illustrates a perspective view showing example ridges forming the internal cam interface 226.

Similar to proximal handle member 130, the proximal handle member 230 can include, from its proximal end towards its distal end: fluid fitting 235, proximal portion 236, recess 237 for coupling with a tool conduit, elongate slot 232, support annulus 233, and external cam interface 231. Proximal portion 236 can comprise a flexible length of tubing as discussed above or can comprise a rigid shaft. If proximal portion 236 comprises a rigid shaft, the fluid fitting 235 can be at a proximal end of the rigid shaft and can move relative to the casing 210 during motion of the proximal handle member 230. As described above, the external cam interface 231 can be positioned at least partly within the actuation sleeve 220. The external cam interface 231 can engage the internal cam interface 226 of the actuation sleeve 220 to form a motion transmitting interface for transmitting rotational or linear motion of the actuation sleeve 220 to the proximal handle member 230.

Similar to the distal handle member 140, the distal handle member 240 can include a proximal shaft 243 positioned partially within the actuation sleeve 220 and partially within an internal receiving volume 239 of the proximal handle member 230. The proximal shaft 243 can have a recess or aperture 244 sized to accept the prong(s) 214 of the casing 210, thereby fixing the position of the distal handle member 240 relative to the casing 210. The distal handle member 240 can include distal aperture 241 through which the conduit secured to the proximal handle member 230 may extend.

FIG. 2D illustrates an example design for the distal end of the handle relating to markings for providing visual extension distance indicators. Position indicator 242 can line up with (or be positioned between) radially-spaced distance indicators 229 on the actuation sleeve 220. Initially, the tool coupled to handle 205 may be positioned with its distal tip at or near the distal end of a jacket. Rotation of the actuation handle 240 can cause controlled extension of the tool from the jacket, and the radially-spaced distance indicators 229 can provide visual indications of how far the distal tip of the tool is extended beyond the distal end of the jacket. Though illustrated as triangular configurations, other designs may use dots, lines, numerical markings, or a combination of these.

Figure 3B:
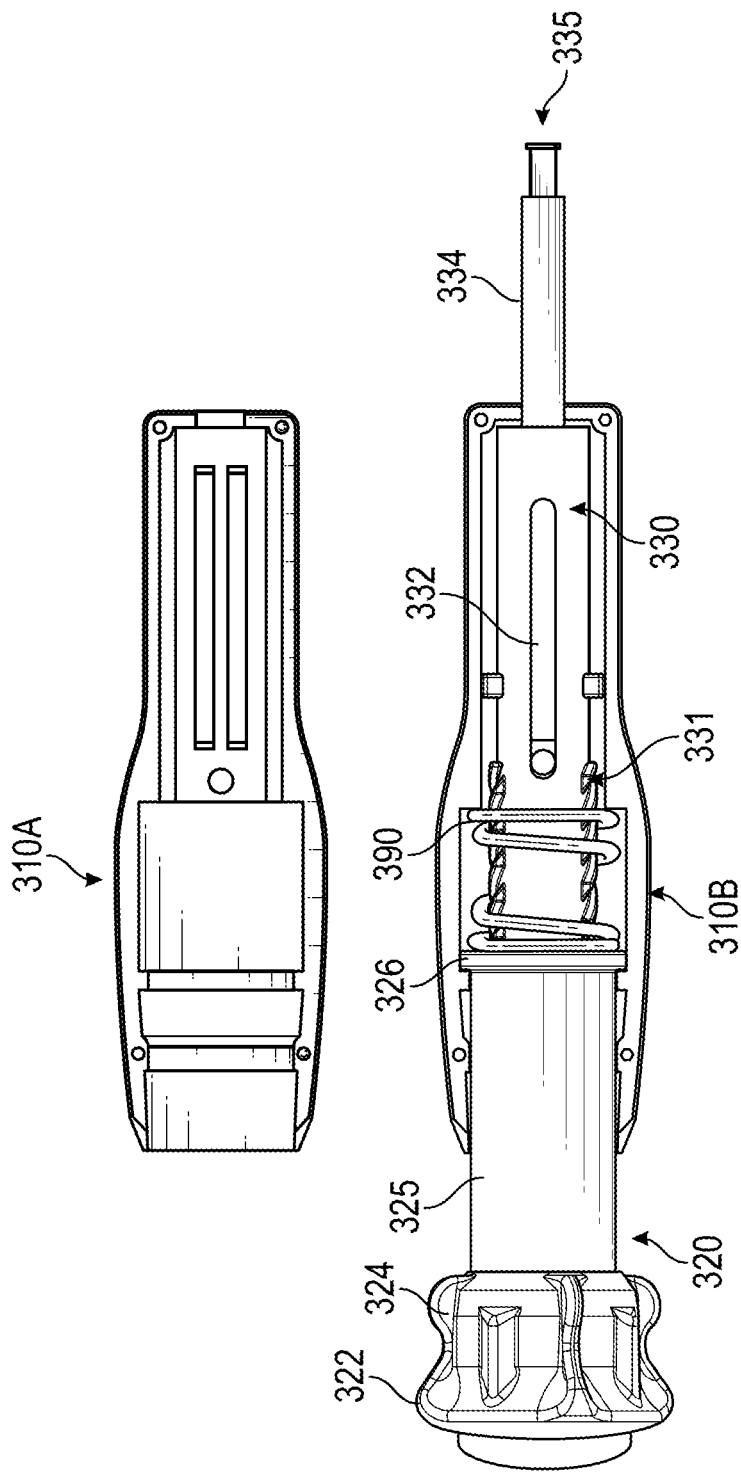

FIGS. 3A and 3B illustrate photos of an example shaft manipulating handle 305 as described herein. FIG. 3A illustrates a disassembled view of the handle 305. FIG. 3B illustrates an assembled view of the handle 305 with the first casing portion 310A removed to show the arrangement of the proximal handle member 330, spring 390, actuation sleeve 320, and distal handle member 340.

As shown in FIG. 3A, similar to handles 105 and 205, the handle 305 can include a casing, actuation sleeve 320, proximal handle member 330, distal handle member 340, and can also include the spring 390. The casing can be formed in first and second portions 310A, 310B that can secure together around the cylindrical body 325 of the actuation sleeve 320 and a distal portion of the proximal handle member 330.

The casing 310A, 310B can provide an internal volume to enclose at least a portion of the moving parts of the handle 305, and can provide an external surface sized and shaped to provide a comfortable surface for grasping with a single hand in some implementations. The casing 310A, 310B can include a distal aperture 311 at its distal end and a proximal aperture 316 at its proximal end. Each half of casing 310A, 310B can include a prong 314A, 314B positioned to extend into the aperture 344 of the distal handle member 340 without occluding a lumen extending through the handle 305. As described above, this can secure the positioning of the distal handle member 340 relative to the casing 410. A portion of the internal volume of the casing can provide a housing 313 for constraining the range of motion of the actuation sleeve 320 and for housing spring 390.

Similar to actuation sleeves 120, 220, actuation sleeve 320 can have a proximal flange 328, a cylindrical body 325 extending from the flange 328 to a rotational wheel grip 324, plunger grip 322, and an internal cam interface 326 (within the actuation sleeve 320 but not visible in FIG. 3A). Rotational wheel grip 324 can be used to facilitate the rotational modality described herein, and the plunger grip 322 can be used to facilitate the plunging modality described herein.

Similar to proximal handle members 130 and 230, the proximal handle member 330 can include, from its proximal end towards its distal end: fluid fitting 335, proximal portion 334, a fastener or fastening mechanism (not shown) for coupling with a tool conduit, a pair of elongate slots 332, support annulus 333, and external cam interface 331. Proximal portion 334 can comprise a rigid shaft having fluid fitting 335 at a proximal end of the rigid shaft. Thus, fluid fitting 335 can move relative to the casing 410 during motion of the proximal handle member 330 and the proximal portion 334 can be sized to pass through the proximal aperture 316 of the casing 310A, 310B. As described above, the external cam interface 331 can be positioned at least partly within the actuation sleeve 320. The external cam interface 331 can engage the internal cam interface 326 of the actuation sleeve 320320 to form a motion transmitting interface for transmitting rotational or linear motion of the actuation sleeve 320 to the proximal handle member 330.

Similar to the distal handle members 140 and 240, the distal handle member 340 can include a proximal shaft 343 positioned partially within the actuation sleeve 320320 and partially within the proximal handle member 330. The proximal shaft 343 can have an aperture 344 sized to accept the prongs 314A, 314B of the casing 310A, 310B, thereby fixing the position of the distal handle member 340 relative to the casing 310A, 310B as shown in FIG. 3B. The distal handle member 340 can include distal aperture 341 through which the conduit secured to the proximal handle member 330 may extend and can include rotation indicator 342.

Turning to FIG. 3B, the actuation sleeve 320, proximal handle member 330, distal handle member 340, and spring 390 are assembled with portion 310B of the casing in place and portion 310A open to show the interior configuration. FIG. 3B illustrates how the spring 390 can be secured within the housing 313 to bias the actuation handle 320 distally with flange 328 pressed against flange 317 of the casing.

FIGS. 4A-4H illustrate another embodiment of a shaft manipulating handle 4405 as described herein. The handle can be used with any of the tools described herein.

Figure 4C:
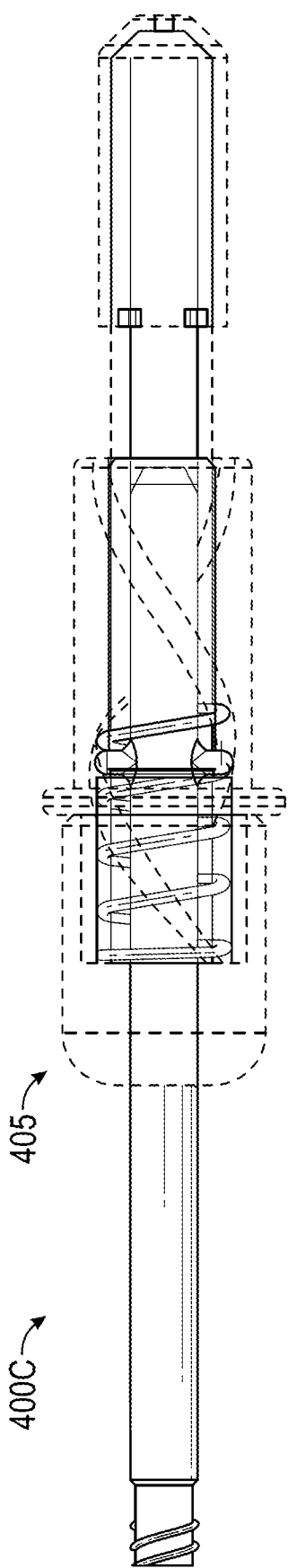
Figure 4D:
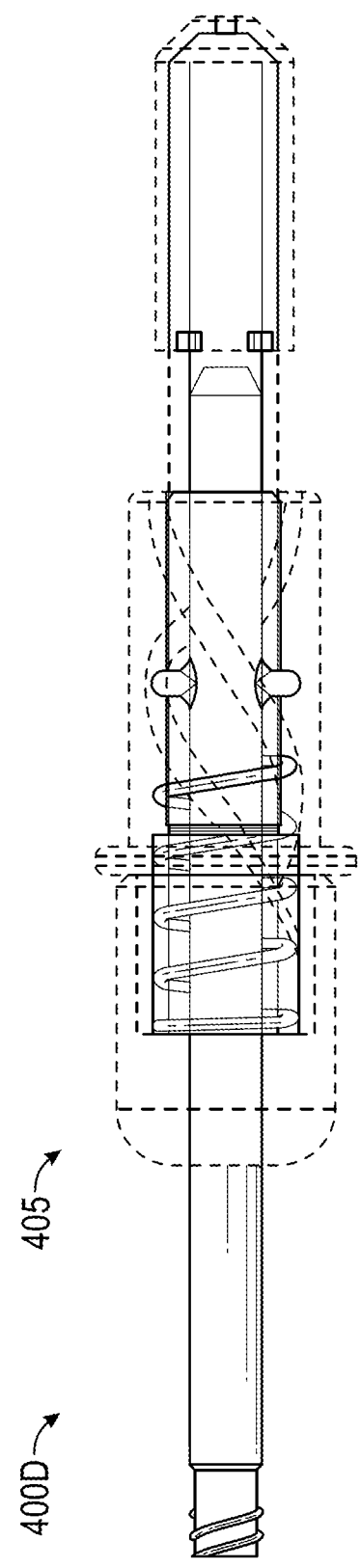

FIGS. 4A-5D illustrate the handle 405 in various states of retraction and extension. FIG. 4A illustrates the handle 405 in a full extension position 400A. In implementations used to drive movement of a biopsy needle through a jacket, for example, the needle would be extended out of the jacket to its maximum extension distance with the handle 405 in the position 400A of FIG. 4A. FIG. 4B illustrates the handle 405 in a retraction position 400B showing the full retraction available via the rotational modality. FIG. 4C illustrates the handle 405 in a full retraction position 400C showing the full retraction available via both the rotational modality and the plunging modality. In the example implementation used to drive movement of the biopsy needle, the needle would be retracted into the jacket to its maximum retraction distance with the handle 405 in the position 400C of FIG. 4C. Upon release of proximally-directed pressure from a grip of the handle, as described more below, the handle 4405 can return to the position 400B of FIG. 4B via force from a biasing element. FIG. 4D illustrates the handle 405 in an intermediate retraction position 400D showing the full retraction available via the plunging modality at an intermediate extension via the rotational modality. FIG. 4D represents one option for dithering a tool into and out of a tissue site in use. Upon release of proximally-directed pressure from the grip of the handle 405 the tool coupled to the handle would be driven distally with force from the biasing element.

Figure 4E:
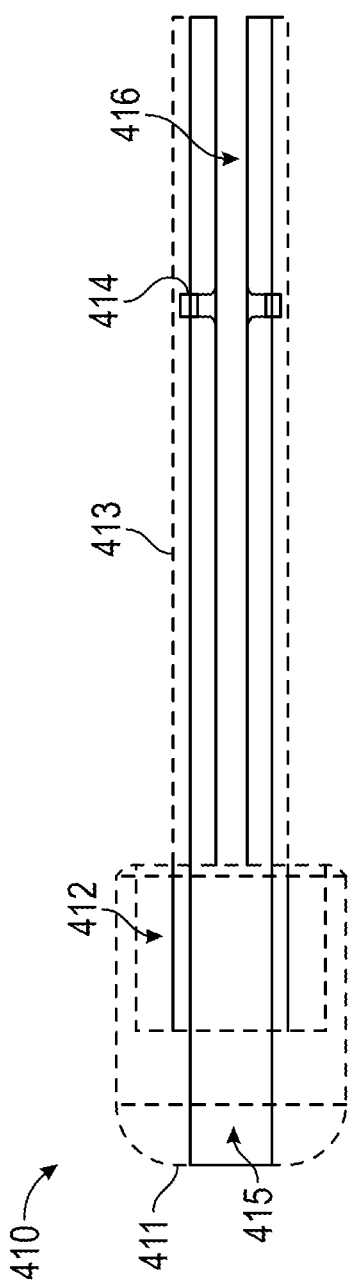
Figure 4F:
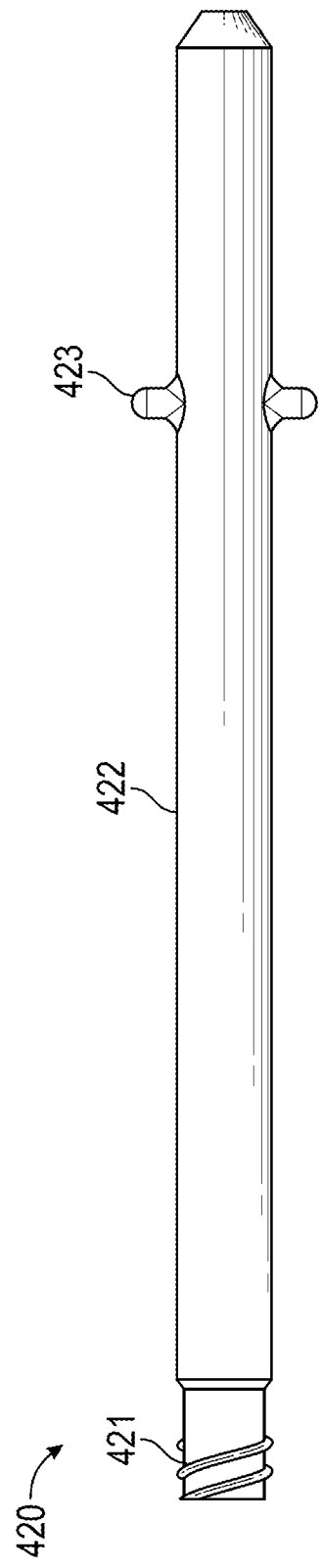
Figure 4G:
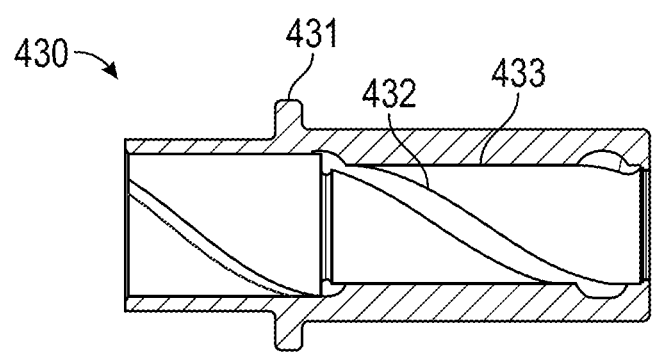
Figure 4H:
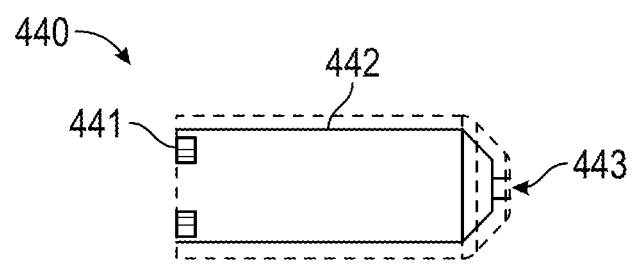

FIGS. 4E-4H illustrate the components of the handle 405. FIG. 4E illustrates the base 410 of the handle, FIG. 4F illustrates the shaft 420 of the handle, FIG. 4G illustrates the cam 430 of the handle, and FIG. 4H illustrates the cap 440 of the handle.

Turning to FIG. 4E, the base 410 includes a grip portion 411 having an internal pocket 412, a body 413 having an inner channel 415, side slots 416, and prongs 414. The grip portion 411 can be rotated or plunged by an operator (human or robotic) to actuate the shaft of a medical instrument coupled to the handle. The base 410 provides a supporting structure for the other components of the handle. For example, the body 413 can extend distally from the grip portion 414 and can be formed as two elongate members each having an arc-shaped cross section. These two elongate members can be separated on opposing sides of the base 410 by gaps to form side slots 416. These slots 416 between the elongated members can slidably engage the cross-pin members 423 of the shaft 420 to prevent the shaft 420 from rotating relative to the base 410. The outer surfaces of the elongate members of the body 413 provide an approximately cylindrical surface for slidably engaging the inner surface 433 of the cam 430 during operation of the handle. The internal pocket 412 provides a space for containing a spring or other biasing element that can push against the flange 431 of the cam 430. The inner channel 415 provides an internal cylindrical pathway within which the shaft 420 can move linearly during use. The prongs 414 can provide a locking interface for the cap 440.

Turning to FIG. 4F, the shaft 420 includes an elongated body 422 with a cross-pin feature 423 and an attachment site 421 for fluidically coupling with an aspiration device. Though not illustrated, in some embodiments the shaft 420 can include an interior pathway or lumen, for example to facilitate provision of aspiration through the lumen of an elongate instrument movable via the handle. The shaft 420 of the handle would be operably coupled to the proximal end of the elongate shaft of the medical instrument to drive extension and retraction of the tool coupled to the distal end of the shaft. Thus, linear motion of this shaft is an objective of the handle.

Turning to FIG. 4G, the cam 430 includes flange 431, inner diameter 433, and a helical groove 432 along its internal surface. The groove 432 can be sized to receive the cross-pin of the shaft 420 and to act as a female internal cam interface. This cam interface can have the illustrated helical groove, or can have any spiral profile to achieve the desired linear motion of the shaft for a given amount of twist on the cam 430. Flange 431 can be used as a grip to facilitate the retraction of the plunging motion of the handle and can engage a biasing element in the pocket 412 to drive extension of the plunging motion upon release of proximally-directed pressure from the flange 431.

Turning to FIG. 4H, the cap 440 fastens to prongs 414 of the base 410 via fastening features 441. Thus, the cap 440 provides a physical stop to prevent the cam 430 from moving off the base 410. The cap 440 can include an aperture 443 through which a tubular jacket of an instrument may be passed, as described above.

Not illustrated in FIGS. 4A-4H is a spring or other biasing mechanism that would be placed in the pocket 412 of the base 410 to return the cam 430 to a full-forward position when no proximal linear force is exerted upon it.

Figure 5A:
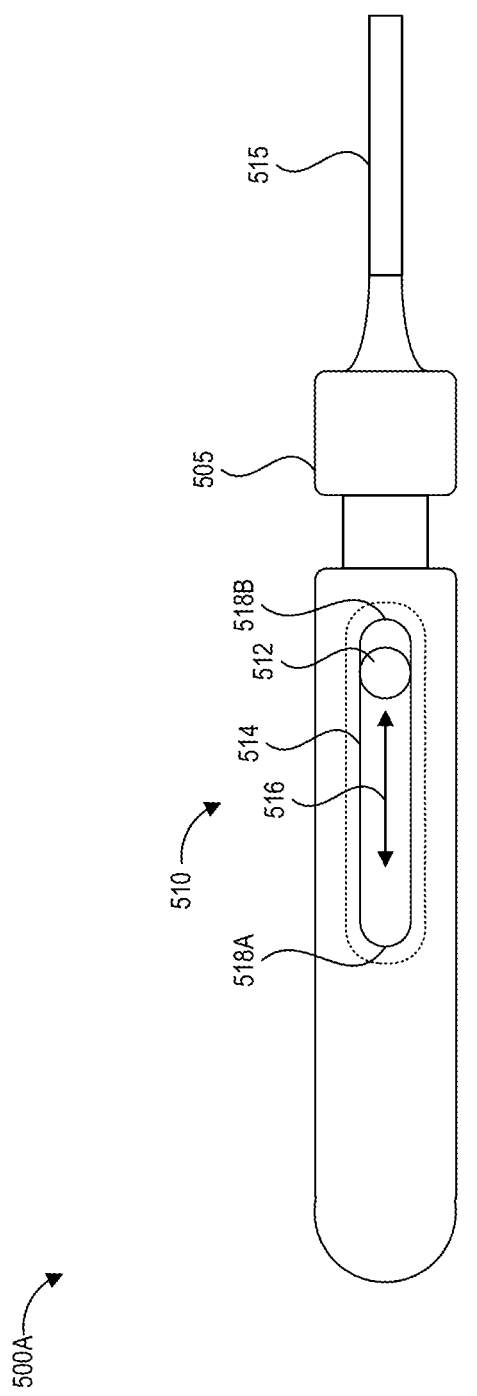
FIGS. 5A-5E illustrate various alternate handle embodiments

FIGS. 5A-5E illustrate various alternate handle embodiments. FIG. 5A illustrates one embodiment of a handle 500A having a jacket 515 extending therefrom and having motion interfaces including a plunging interface 505 and an in-line linear slider 510. As described above, a conduit having a tool at its distal end can be positioned within the jacket 515. In an initial configuration, the distal end of the tool can be positioned at or proximally to the distal end of the jacket. As described above, movement of the tool can be driven by movement of the conduit.

The slider 510 includes a tab 512 slidable within a track 514. The tab 512 can be coupled to an internal drive member that, in turn, is coupled to a proximal end of the conduit. As such, linear motion 516 of the tab 512 can translate 1:1 into extension or retraction of the instrument relative to the distal end of the jacket 515. When the tab 512 is positioned at a proximal end 518A of the track 514 the tool can be in a fully retracted position relative to the jacket 515. When the tab 512 is positioned at the distal end 518A of the track 514 the tool can be in a fully extended position relative to the jacket 515. The tab 512 can be slid to any intermediate position between the proximal and distal ends 518A, 518B and may lock in place. For example, the tab 512 may include a button that, when depressed, allows the sliding motion 516 and that, when released, locks the slider. Although not illustrated, distance markings can be provided along the handle at or near the track 514 to indicate how far the tool is extended.

The plunging interface 505 can be retracted proximally to withdraw an extended tool proximally into the jacket 515 and may be biased to return to the illustrated extended position upon release of force from the plunging interface 505. Thus, the plunging interface 505 can be used to actuate a dithering motion as described above. In some embodiments the plunging interface 505 can extend the tool and be biased toward the retracted position. As the plunging interface 505 is actuated, the tab 512 can slide through the track 514 to provide a visual indication of the extension and/or retraction distance of the tool.

Figure 5B:
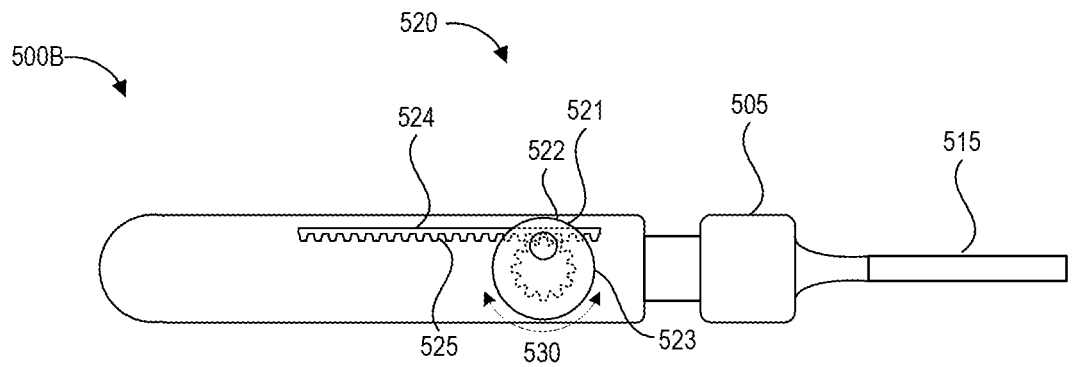
Figure 5C:
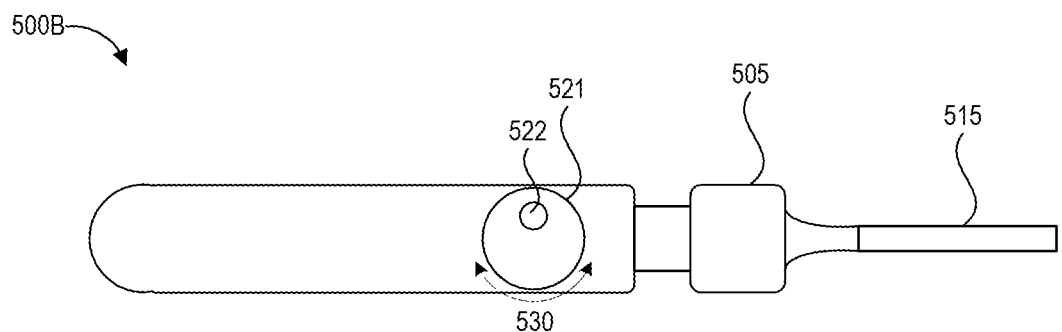
Figure 5D:
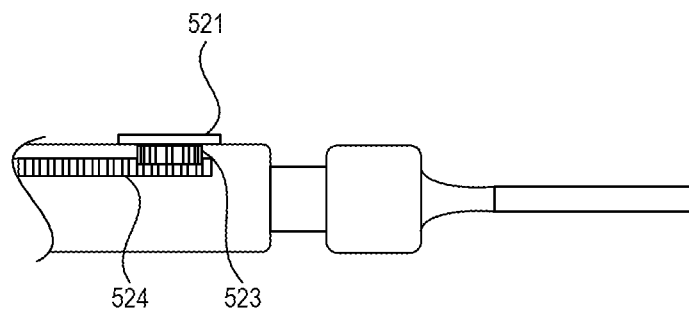

FIGS. 5B-5D illustrate another embodiment of the handle 500B having the jacket 515 and the plunging interface 505, and also having a rack and pinion actuator 520. As described above, the tool and conduit can be positioned at least partly within the jacket 515 and the rack and pinion actuator 520 can drive the fine-control extension and retraction of the tool.

FIG. 5B depicts a cutaway top view of the handle 500B and shows the outline of both the exterior and interior components of the rack and pinion actuator 520, with dashed lines showing the outline of elements positioned behind other elements (from the perspective of the illustrated viewpoint). The rack and pinion actuator 520 includes a rotational wheel 521 having a detent 522 to facilitate grip during rotation by a user. Alternate embodiments could additionally or alternatively include ridges around the outer circumference of the wheel 521.

The wheel 521 is coupled to a gear 523 having a number of radial teeth. These teeth can engage corresponding teeth 525 in a rack 524 to actuate linear motion along the longitudinal axis of the handle 500B in response to rotation 530 of the wheel 521. In some embodiments, the rack 524 can move linearly within the handle 500B and can be coupled to the internal drive member that, in turn, is coupled to the proximal end of the conduit. Thus, movement of the rack 524 can translate 1:1 into extension or retraction of the instrument relative to the distal end of the jacket 515. In other embodiments, the wheel 521 and gear 523 can move linearly along the handle and the gear 523 can be coupled to the internal drive member to actuate the tool extension and retraction.

As shown in the exterior top view depicted in FIG. 5C, the wheel 521 is located on the outside of the handle 500B. As shown in the cutaway side view depicted in FIG. 5D, the gear 523 and rack 524 are positioned within the handle 500B.

Similar to the handle 500A, the plunging interface 505 of the handle 500B can be retracted proximally and/or extended distally to withdraw or extend the tool relative to the jacket 515 and may be biased to return to its initial position upon release of force from the plunging interface 505. Thus, the plunging interface 505 can be used to actuate a dithering motion as described above. As the plunging interface 505 is actuated, the wheel 521 may rotate and/or the entire rack and pinion actuator 520 can move proximally and distally. This can be accompanied by distance markings to provide a visual indication of the extension and/or retraction distance of the tool.

Figure 5E:
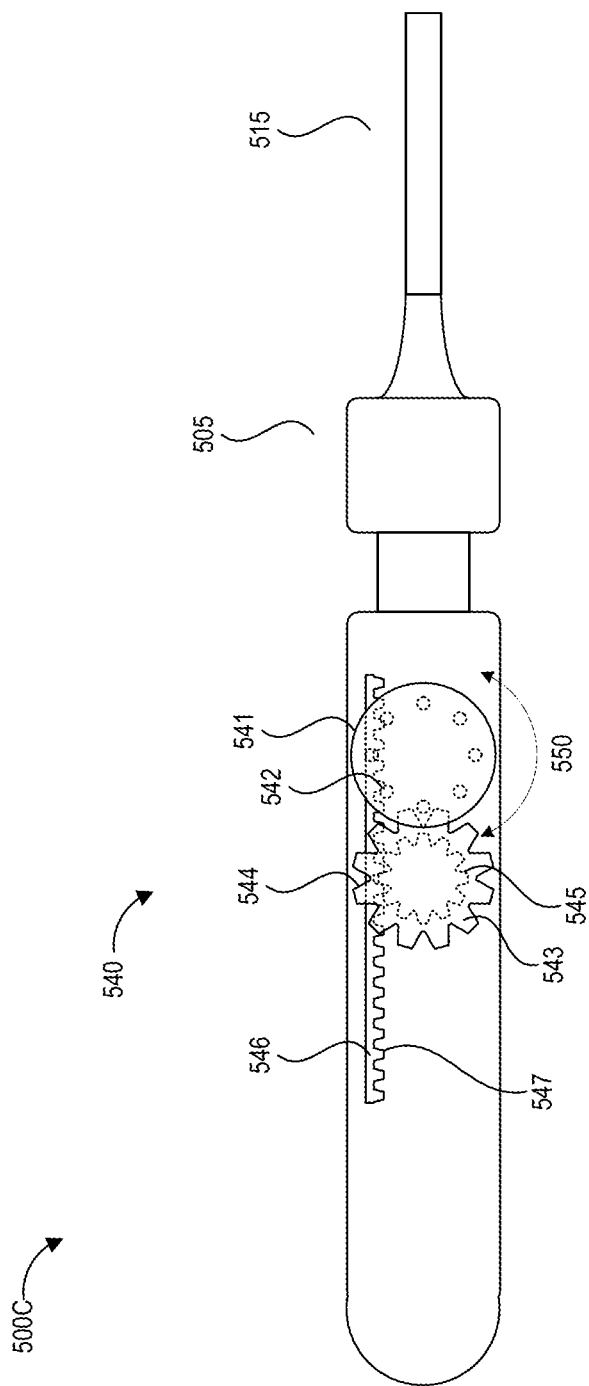

FIG. 5E illustrates another embodiment of the handle 500B having the jacket 515 and the plunging interface 505, and also having an incremental rotation actuator 540. FIG. 5E depicts a cutaway top view of the handle 500C and shows the outline of both the exterior and interior components of the rack and incremental rotation actuator 540, with dashed lines showing the outline of elements positioned behind other elements (from the perspective of the illustrated viewpoint). As described above, the tool and conduit can be positioned at least partly within the jacket 515 and the rack and incremental rotation actuator 540 can drive the fine-control extension and retraction of the tool.

The incremental rotation actuator 540 includes a rotational wheel 541 having a number of spokes 542 extending inwardly (e.g., toward the interior of the handle 500C) from the wheel 541. Though not illustrated, the top or user-facing side of the wheel 541 can have a detent and/or ridges around its circumference to facilitate grip during rotation by a user, similar to the wheel 521 of FIG. 5C.

The incremental rotation actuator 540 also includes a gear 543 and a rack 546. The gear 543 can include a number of first teeth 544 that are engaged by the spokes 542. As the wheel 541 is rotated 550 and a spoke 542 pushes one of the first teeth 544, the gear 543 can also rotate by a predetermined amount corresponding to the number of the first teeth 544 and the number of spokes 542. As the gear 543 rotates, a number of second teeth 545 also rotate. The second teeth 545 can engage the teeth 547 of the rack 546 to move the rack 546 linearly within the handle 500C. The rack 546 can be coupled to the internal drive member that, in turn, is coupled to the proximal end of the conduit. Thus, movement of the rack 524 can translate 1:1 into extension or retraction of the instrument relative to the distal end of the jacket 515.

In some embodiments, ten degrees of rotation can correspond to a 5 mm movement of the tool. Other embodiments can be designed to correlate other degrees of rotation with other movement distances. As such, the handle 500C can provide for movement of the tool in predetermined increments based on the rotation 550 of the wheel 541.

Similar to the handle 500A, the plunging interface 505 of handle 500C can be retracted proximally and/or extended distally to withdraw or extend the tool relative to the jacket 515 and may be biased to return to its initial position upon release of force from the plunging interface 505. Thus, the plunging interface 505 can be used to actuate a dithering motion as described above. As the plunging interface 505 is actuated, the wheel 541 may rotate and/or the entire incremental rotation actuator 540 can move proximally and distally. This can be accompanied by distance markings to provide a visual indication of the extension and/or retraction distance of the tool.

Overview of Example Robotic Surgical Systems

Figure 6:
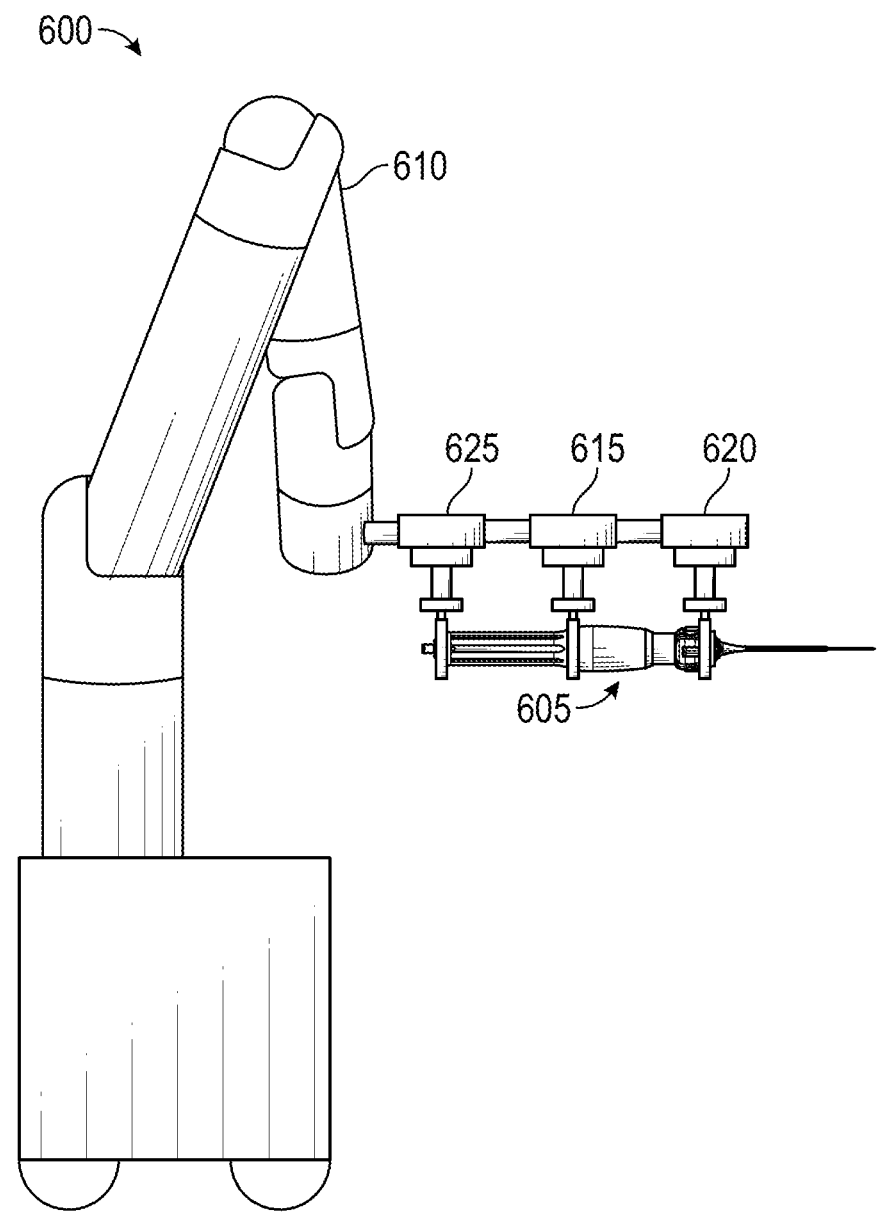
FIG. 6 depicts a schematic diagram of a robotic surgical system for actuating a handle as described herein.

FIG. 6 depicts a schematic diagram of a robotic surgical system 600 for actuating a handle 605 as described herein. Though shown with a particular configuration of the handle 605, any of the described handles can be used with such a system 600. The instrument handle may have a barcode, radio-frequency identifier (RFID), or other suitable identifier to enable the robotic surgical system 600 to identify the handle.

The example robotic system 600 includes an articulated arm 610 configured to locate, and maintain positioning of, the handle 605. At a distal end of the arm 610 are a first grip portion 625 for controlling aspiration or administering therapeutics and two additional grip portions 615, 620 that can open to receive the handle 5605 and close around respective portions of the handle 605. The first grip portion 625 can include one or more actuators for gripping and controlling a source of negative (or positive pressure) and/or therapeutics. For example, the first grip portion 625 can include a first actuator for attaching a syringe and a second actuator for robotically controlling a plunger of the syringe.

The second grip portion 615 may maintain a stationary grip and positioning on the handle 605 to provide stability. The third grip portion 620 can be configured to effect the rotational modality of the handle described herein by rotating a wheel or grip of the handle. Further, the third grip portion 620 can be configured to move laterally with respect to the longitudinal axis of the handle to provide the plunging modality described herein. In other embodiments the second grip portion 615 can move to effect the plunging and rotational modalities, alone or in combination with movement of the third grip portion 620. The grip portions 615, 620, 625 can be driven by one or more motors and appropriate actuation mechanisms.

The robotic surgical system 600 is shown with one embodiment of a handle 605 as described herein. Other embodiments of the robotic surgical system 600 can be used to operate variations of the disclosed handle embodiments, for example including different actuation interfaces (e.g., two plunging interfaces, two rotational interfaces, etc.). The robotic surgical system 600 can be configured to control and any or all of the handle actuations, for example the fine control extension/retraction only, dithering only, or both as described above.

The robotic surgical system 600 can include a processor(s) and memory. The memory can store instructions for operation of the various components of the robotic surgical system 600 as well as data produced and used during a surgical procedure. The processor(s) can execute these instructions and process such data to cause operation of the system 600. Although not illustrated, the robotic surgical system 600 can include other components, for example one or more input devices for receiving user input to control motion of surgical instruments (e.g., joysticks, handles, computer mice, trackpads, and gesture detection systems), instrument drivers to effect the motion of the surgical instruments, an additional grip portion for securing and controlling motion of an aspiration device coupled to the handle, a display screen, and the like.

Overview of Example Methods of Use

Figure 7:
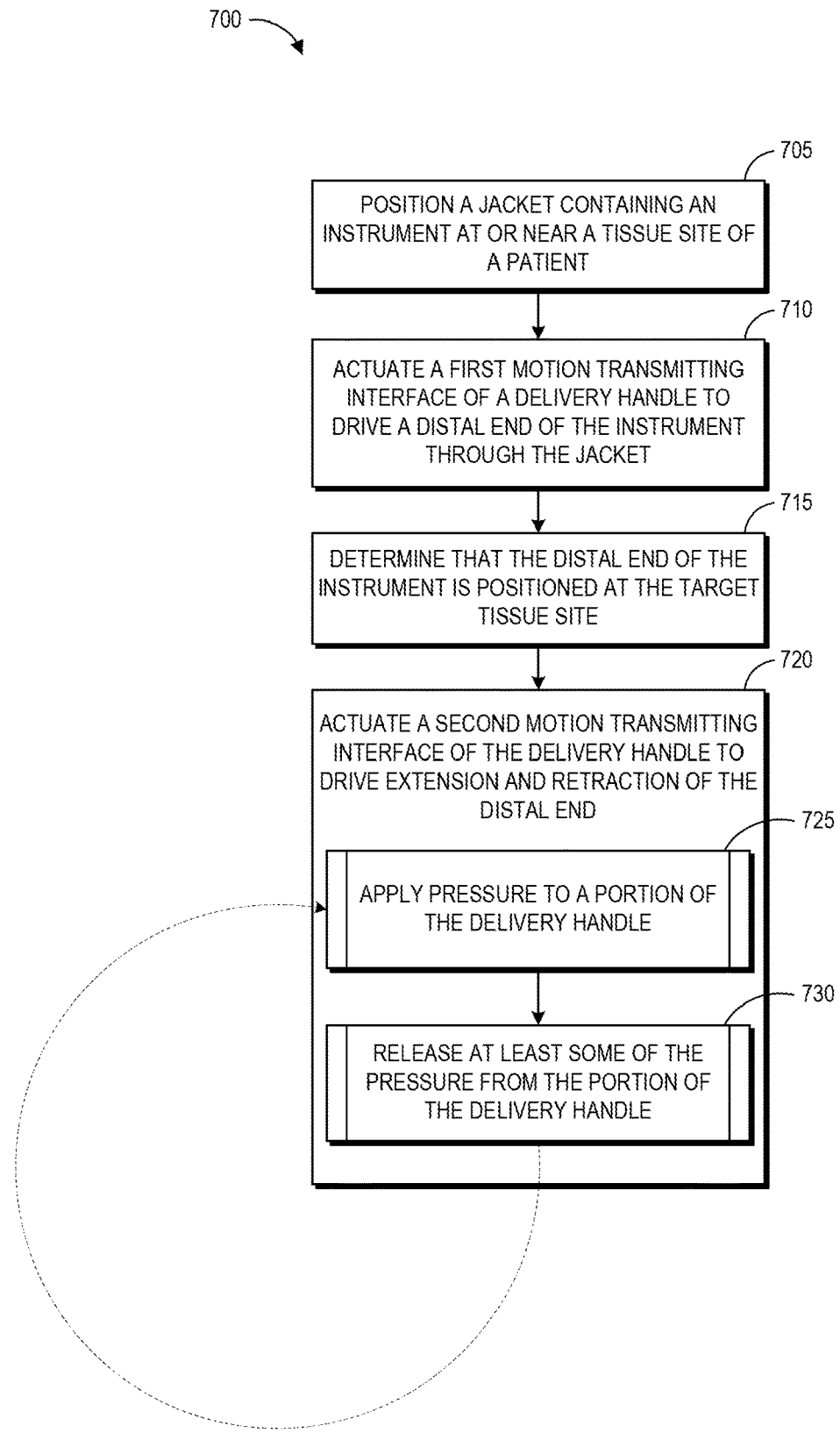
FIG. 7 depicts a flowchart of an embodiment of a process for driving movement of a medical instrument using a handle as described herein.

FIG. 7 depicts a flowchart of an embodiment of a process 700 for driving movement of a medical instrument using the handles described herein, for example, handles 105, 205, 305, 405, 500A-500C, and 605 as described above). The process 700 can be implemented by a human operator manually manipulating the handle, a robotic control system operator (such as system 600 described above) mechanically manipulating the handle as directed by a human operator or autonomously, or a combination thereof.

At block 705, the operator (e.g., a human operator or autonomous surgical robot) can position a jacket containing an instrument at or near a tissue site of a patient. As described above, the instrument can be positioned with its distal tip at or near the distal end of the jacket 150 and a conduit 154 or shaft can extend from the proximal end of the tool through the jacket. The jacket can be inserted through the working channel of an endoscope such as a bronchoscope in some embodiments, and the tool can be a needle, brush, forceps, or the like. The conduit can be coupled to a handle 105, 205, 305, 405, 500A-500C, 605 for driving linear motion of the conduit relative to the jacket.

At block 710, the operator can actuate a first motion transmitting interface of the delivery handle 105, 205, 305, 405, 500A-500C, 605 coupled to the instrument to drive the distal end of the instrument to advance through the jacket. As described above and shown in the example of FIG. 1A, this can involve actuation of a rotational modality of the handle, for example by rotational grip 122, 222, 322 or actuation of the motion mechanisms described with respect to handles 500A-500C. Actuation of such a modality can allow the operator to exert fine control over extending the distal tip of the instrument out from the distal end of the jacket. In some procedures, this can involve extending the distal tip of the instrument until it has pierced patient tissue.

At block 715, the operator can determine that the distal end of the instrument is positioned at the target tissue site. In some implementations, a physician may view an image or video of the tissue site via an imaging device at the distal end of an endoscope working channel and may visually confirm that the instrument is positioned at or within the target tissue site. For example, this can be accomplished via fluoroscopy. In some implementations, the physician may view a rendering or model of the positioning of the instrument relative to the patient tissue site to make this determination, for example as output from a robotic bronchoscopy navigation system. In some embodiments block 715 can be performed programmatically via automated image analysis and/or navigation.

At block 720, the operator can actuate a second motion transmitting interface of the delivery handle 105, 205, 305, 405, 500A-500C, 605 to drive extension and retraction of the distal end of the instrument. As described above and shown in the example of FIG. 1B, this can involve actuation of a plunging modality, for example by plunging grip 122, 222, 322.

As shown by sub-blocks 725 and 730, actuation of the second motion transmitting interface can involve a first step of retraction and a second step of extension. At block 725, the operator can apply pressure to a portion of the delivery handle to (1) compress a biasing element of the second motion transmitting interface, and (2) drive retracting motion of the instrument to withdraw the distal end of the instrument from the tissue site. At block 730, the operator can release at least some of the pressure from the portion of the delivery handle to allow expansion of the second motion transmitting interface to drive the distal end of the into the tissue site. In other embodiments, the handle can be structured such that application of pressure results in extension of the tool and release of the pressure retracts the tool. Repetition of blocks 725 and 760 can generate a dithering motion of the tool through repeated extension and retraction which, as described above, may be beneficial in tissue sampling.

After completion of the process 700 the instrument can be withdrawn back into the jacket, for example via the first motion transmitting interface, and the jacket can be withdrawn from the patient tissue site. Any obtained sample can be expelled from the instrument for the desired analysis.

Implementing Systems and Terminology

Implementations disclosed herein provide systems, methods and apparatus for actuating extension and retraction of a remotely-disposed instrument by way of linear motion of a shaft of the instrument secured within a handle.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A handle configured to drive movement of a bronchoscopy instrument, the handle extending along a longitudinal axis between a proximal end and a distal end of the handle and comprising:
   a casing having an inner surface defining an internal volume including a biasing element housing portion;
   a proximal handle member positioned at least partly within a proximal portion of the internal volume of the casing and including a first helical cam interface, the proximal handle member configured to couple to a proximal end of an elongate channel extending beyond the distal end of the handle with a distal end of the elongate channel coupled to the bronchoscopy instrument;
   an actuation sleeve positioned at least partly within a distal portion of the internal volume of the casing and including:
      a proximal portion having a second helical cam interface engaging the first helical cam interface,
      a rotation grip extending distally from the proximal portion of the actuation sleeve, and
      a plunger grip formed by a distal surface of the actuation sleeve, wherein the plunger grip is positioned such that a pressure applied to the plunger grip of the actuation sleeve toward the proximal portion drives, via the engaging of the first helical cam and the second helical cam, a linear motion of the actuation sleeve and the proximal handle member and drives compression of a biasing element; and
   the biasing element having a first end secured within the biasing element housing portion of the casing and a second end engaging the proximal portion of the actuation sleeve.

2. The handle of claim 1, wherein the biasing element comprises a spring positioned to compress and expand along the longitudinal axis during movement of the actuation sleeve via the plunger.

3. The handle of claim 1, wherein the second helical cam interface engaging the first helical cam interface is configured to translate rotation of the rotation grip into linear motion of the proximal handle member along the longitudinal axis of the handle, and wherein the linear motion of the proximal handle member is configured to drive the movement of the instrument via the elongate channel.

4. The handle of claim 3, wherein the actuation sleeve is configured to simultaneously impart linear motion and rotation motion of the actuation sleeve into linear motion of the proximal handle member.

5. The handle of claim 1, wherein:
   the second helical cam interface engaging the first helical cam interface translates proximal retraction of the plunger grip into proximal motion of the proximal handle member along the longitudinal axis of the handle, and wherein the linear motion of the proximal handle member is configured to drive proximal retraction of the instrument via the elongate channel; and
   the biasing element is positioned to compress as the plunger grip is retracted proximally such that, upon release of the plunger grip, a bias of the biasing element drives distal linear motion of the proximal handle member along the longitudinal axis of the handle, and wherein the linear motion of the proximal handle member is configured to drive distal extension of the instrument.

6. The handle of claim 1, further comprising:
   a distal handle member positioned within the casing; and
   an internal receiving portion at a distal portion of the proximal handle member, wherein a proximal portion of the distal handle member is positioned within the internal receiving portion.

7. The handle of claim 6, further comprising a lumen extending through the handle along the longitudinal axis, wherein a distal portion of the lumen extends through the distal handle member and a proximal portion of the lumen extends through the proximal handle member.

8. The handle of claim 7, further comprising a distal aperture formed in a distal end of the distal handle member, wherein the lumen is sized to accommodate positioning of the elongate channel within the lumen, and wherein the distal aperture is sized to accommodate passage of the elongate channel through the distal aperture.

9. The handle of claim 6, further comprising:
   a peg extending inwardly within the internal volume of the casing;

an aperture in the distal handle member sized and positioned to receive the peg, wherein the distal handle member is fixed relative to the casing via the received peg; and an elongate slot formed in a wall of the proximal handle member, wherein the elongate slot is sized and positioned to slide around the peg with the wall of the proximal handle member positioned between the casing and the distal handle member.

10. The handle of claim 1, further comprising a fluid fitting at a proximal end of the proximal handle member, the fluid fitting configured to couple to an aspiration device or a respiration device.

11. The handle of claim 10, further comprising a flexible shaft portion of the proximal handle member positioned between the second helical cam interface and the fluid fitting, wherein the fluid fitting is fixed relative to the casing.

12. The handle of claim 11, wherein the flexible shaft portion comprises a length of coiled conduit.

13. The handle of claim 10, further comprising a rigid shaft portion of proximal handle member extending between the second helical cam interface and the fluid fitting, wherein a proximal portion of rigid shaft portion is coupled to the fluid fitting, and wherein the rigid shaft portion is slidably engaged with a proximal aperture of the casing.

14. The handle of claim 1, further comprising a rack and pinion actuator, the rack and pinion actuator configured to impart fine control over the linear motion of the proximal handle member.

15. A handle configured to drive movement of an instrument, the handle extending along a longitudinal axis between a proximal end and a distal end of the handle and comprising:
　a casing having an inner surface defining an internal volume;
　a proximal handle member configured to couple to a channel extending beyond the distal end of the handle to the instrument, the proximal handle member including a first helical cam interface; and
　an actuation sleeve including:
　　a proximal portion having a second helical cam interface engaging the first helical cam interface of the proximal handle member;
　　a rotational motion transmitting interface coupling the proximal handle member to the actuation sleeve and configured to translate rotational motion of the actuation sleeve into linear motion of the proximal handle member along the longitudinal axis of the handle; and
　　a plunging mechanism configured to drive distal movement of the proximal handle member along the longitudinal axis via the rotational motion transmitting interface, the plunging mechanism comprising a biasing element positioned to compress and expand along the longitudinal axis during movement of the actuation sleeve.

16. The handle of claim 15, wherein expansion of the biasing element drives the distal movement of the proximal handle member along the longitudinal axis.

17. The handle of claim 16, wherein the plunging mechanism comprises a grip of the actuation sleeve positioned such that pressure applied to the grip drives proximal movement of the actuation sleeve along the longitudinal axis and drives compression of the biasing element.

18. The handle of claim 17, wherein the rotational motion transmitting interface coupling the proximal handle member to the actuation sleeve is configured to transmit the proximal and distal movement of the actuation sleeve to the proximal handle member.

19. The handle of claim 15, wherein the biasing element comprises one of a spring, opposing magnets, hydraulic fluid, and a shape memory alloy.

20. An apparatus configured to drive movement of an instrument, the apparatus extending along a longitudinal axis between a proximal end and a distal end of the apparatus and comprising:
　a casing having an inner surface defining an internal volume;
　a proximal handle member positioned at least partly within a proximal portion of the internal volume of the casing and including a first helical cam interface;
　an actuation sleeve configured to impart rotational and linear motion of the actuation sleeve along the longitudinal axis to linear motion of the instrument, the actuation sleeve including:
　　a proximal portion with a second helical cam configured to engage with the first helical cam of the proximal handle member; and
　　a grip having a rotational interface and a plunging interface, the grip extending beyond a distal end of the casing; and
　a biasing element within the internal volume, the biasing element positioned to compress and expand along the longitudinal axis during movement of the actuation sleeve wherein expansion of the biasing element drives linear movement of the actuation sleeve in a proximal direction along the longitudinal axis.

* * * * *